United States Patent [19]

Gaisford et al.

[11] Patent Number: 5,103,181

[45] Date of Patent: Apr. 7, 1992

[54] COMPOSITION MONITOR AND MONITORING PROCESS USING IMPEDANCE MEASUREMENTS

[75] Inventors: Scott G. Gaisford, Brisbane; John P. Watjen, Sunnyvale, both of Calif.; Bjorn G. Bjornsen, Sandnes, Norway

[73] Assignee: Den Norske Oljeśelskap a.s., Stavonger, Norway

[21] Appl. No.: 254,415

[22] Filed: Oct. 5, 1988

[51] Int. Cl.[5] .......................................... G01N 22/00
[52] U.S. Cl. ................................. 324/637; 324/639; 324/640; 324/642; 324/643; 324/645
[58] Field of Search .............. 324/58 R, 58 B, 58.5 R, 324/58 A, 58.5 A, 633, 634, 635, 637, 639–643, 645–648; 73/61 R, 61.1 R; 333/248

[56] References Cited

U.S. PATENT DOCUMENTS

| | | |
|---|---|---|
| 1,726,721 | 4/1926 | Schullstrom . |
| 1,877,810 | 9/1926 | Chamberlain . |
| 2,020,847 | 1/1931 | Mitereff . |
| 2,099,687 | 11/1935 | Hartig . |
| 2,124,029 | 6/1936 | Conklin et al. . |
| 2,169,174 | 10/1936 | Ziebolz . |
| 2,222,450 | 7/1938 | Trost . |
| 2,297,393 | 10/1939 | Deserno . |
| 2,323,675 | 9/1937 | Rand . |
| 2,386,830 | 9/1942 | Wright . |
| 2,548,598 | 2/1944 | Feiker, Jr. . |

(List continued on next page.)

FOREIGN PATENT DOCUMENTS

| | | |
|---|---|---|
| 0268399 | 5/1988 | European Pat. Off. . |
| 0039448 | 4/1981 | Japan .......................... 324/58.5 R |
| 1122987 | 8/1968 | United Kingdom . |
| 2210461 | 8/1988 | United Kingdom . |

OTHER PUBLICATIONS

Borders et al., (Sep., 1983), *Microvascular Research*, 26:347–350, An Improved Sensor Head for Cross-Correlation Intravital Velocimetry.

Hammer et al., (May, 1983), *J. Phys. E. Sci. Instrument*, 16:438–443, The Spatial Filtering Effect of Capacitance Transducer Electrodes.

Herrman et al., (Jul., 1987), *Microvascular Research*, 34:13–28, Precision Velocimetry with Digital Cross-Correction for Flow Measurements During Thrombus Growth.

Intaglietta et al., (Jul., 1987), *Microvascular Research*, 34:108–115, Capillary Video Red Blood Cell Velocimetry by Cross-Correlation and Spatial Filtering.

Pittman et al., (Nov., 1986), *Microvascular Research*, 32:371–388, Estimation of Red Cell Flow in Microvessels: Consequences of the Baker-Wayland Spatial Averaging Model.

*Primary Examiner*—Kenneth Weider
*Assistant Examiner*—Jack B. Harvey
*Attorney, Agent, or Firm*—Irell & Manell

[57] ABSTRACT

Radio frequency bridge techniques are used to parameterize the complex dielectric properties of solids, liquids, gasses and mixtures thereof. This parameterization is performed in an electrically isolated, physically open structure which allows continuous or batch monitoring of the materials and their mixtures. A method and apparatus are provided for measuring the composition of mutlicomponent process streams flowing in pipes or ducts. The method uses the pipe in which the mixture flows as a waveguide in which propagating radio frequency electromagnetic energy is induced through dielectric loaded apertures. The dielectric measurement is performed in an electrically isolated, flow through test section which induces constructive or destructive interference patterns at characteristics frequencies. The characteristic frequency determines the dielectric constant of the mixture. The dielectric properties are used in turn to determine mixture composition. A density measurement is also provided for three comiponent strams such as oil, water, and gas. Temperature and pressure measurements are made to correct for temperature and pressure induced variations in calibrated component impedance and density values.

61 Claims, 29 Drawing Sheets

U.S. PATENT DOCUMENTS

| | | | |
|---|---|---|---|
| 2,736,867 | 12/1945 | Montgomery . | |
| 2,792,548 | 5/1945 | Hershberger . | |
| 3,136,946 | 9/1960 | Le Vine . | |
| 3,475,316 | 6/1965 | De Vittorio . | |
| 3,498,112 | 3/1970 | Howard | 73/61.1 |
| 3,586,971 | 6/1971 | Bosisio . | |
| 3,612,996 | 10/1971 | Bleackley . | |
| 3,688,188 | 8/1972 | Bak et al. | 324/58.5 C |
| 3,720,890 | 3/1973 | Anderson | 324/58.5 B X |
| 3,762,221 | 10/1973 | Coulthard | 73/194 E |
| 3,816,811 | 6/1974 | Cmelik | 324/61 R |
| 3,826,978 | 6/1974 | Kelly | 324/58.5 A |
| 3,826,980 | 6/1974 | Deichelmann et al. . | |
| 3,858,446 | 1/1975 | Flemons . | |
| 3,883,798 | 5/1975 | Free | 324/58.5 C |
| 3,889,182 | 6/1975 | Easley et al. | 324/58.5 A |
| 3,897,798 | 8/1975 | De Vale | 324/61 R X |
| 3,967,500 | 7/1976 | Forster | 73/194 E |
| 4,097,801 | 6/1978 | Freeman et al. . | |
| 4,104,585 | 8/1978 | Schofield | 324/58.5 C |
| 4,124,475 | 11/1978 | Zetter et al. | 204/195 R |
| 4,248,085 | 2/1981 | Coulthard | 73/861.06 |
| 4,254,470 | 3/1981 | Jordan . | |
| 4,257,275 | 3/1981 | Kurita et al. | 73/861.06 |
| 4,266,188 | 5/1981 | Thompson | 324/65 R |
| 4,266,425 | 5/1981 | Allport et al. | 73/61 R |
| 4,285,046 | 8/1981 | Henry . | |
| 4,288,741 | 9/1981 | Dechene et al. | 324/61 R |
| 4,301,400 | 11/1981 | Paap | 324/58.5 A |
| 4,327,323 | 4/1982 | Walker | 324/61 R |
| 4,340,938 | 7/1982 | Rosso | 73/61.1 R X |
| 4,345,204 | 8/1982 | Shelley | 324/61 R |
| 4,370,611 | 1/1983 | Gregory et al. | 324/61 R |
| 4,380,924 | 4/1983 | Nakamoto et al. | 73/19 |
| 4,387,165 | 6/1983 | Youngblood | 324/71.6 X |
| 4,402,230 | 9/1983 | Raptis | 73/861.06 |
| 4,417,584 | 11/1983 | Cathignol et al. | 73/861.25 X |
| 4,423,623 | 1/1984 | Ho et al. | 73/61 R |
| 4,429,273 | 1/1984 | Mazzagatti | 324/61 R |
| 4,441,362 | 4/1984 | Carlson | 73/61.1 R X |
| 4,458,524 | 7/1984 | Meador et al. | 73/61.1 R |
| 4,503,383 | 3/1985 | Agar et al. . | |
| 4,543,191 | 9/1985 | Stewart et al. | 73/61 R X |
| 4,548,506 | 10/1985 | Elson | 356/446 |
| 4,555,661 | 11/1985 | Benson et al. | 324/61 R |
| 4,559,493 | 12/1985 | Goldberg et al. | 324/61 R |
| 4,580,444 | 4/1986 | Abts et al. . | |
| 4,588,970 | 5/1986 | Donecker et al. . | |
| 4,596,136 | 6/1986 | Zacharias . | |
| 4,604,904 | 8/1986 | Massen . | |
| 4,651,085 | 7/1984 | Sakurai et al. | 324/58.5 R |
| 4,693,319 | 9/1987 | Amemiya | 73/861.25 X |
| 4,708,021 | 11/1987 | Braun et al. | 73/861.06 |
| 4,720,677 | 1/1988 | Donecker et al. . | |
| 4,760,742 | 8/1988 | Hatton . | |

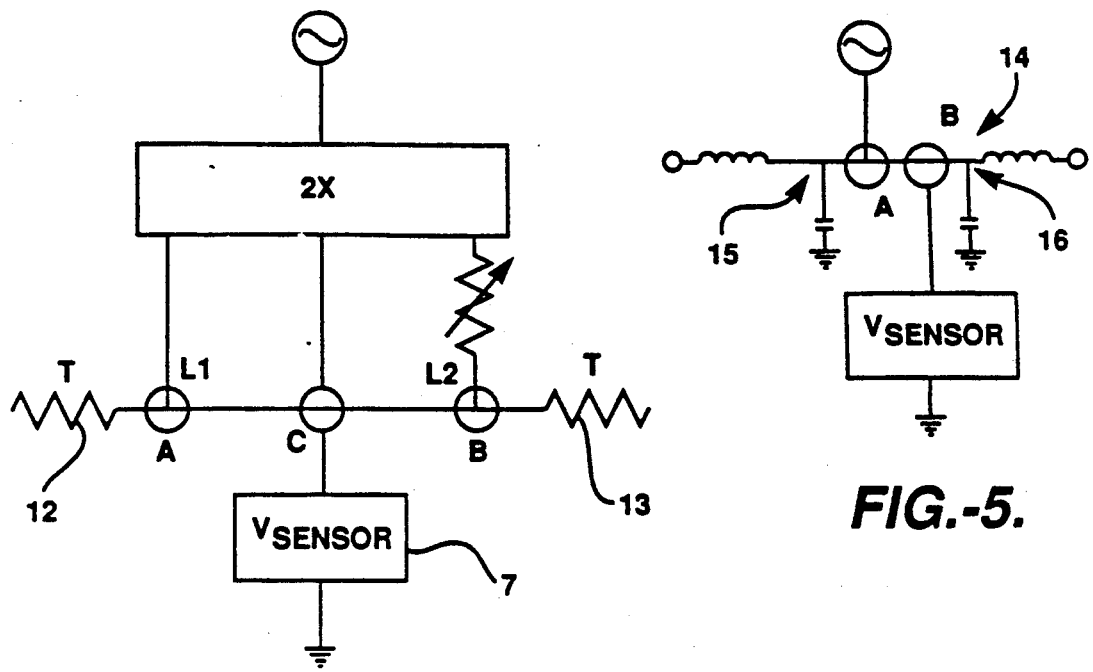
FIG.-4.
FIG.-5.
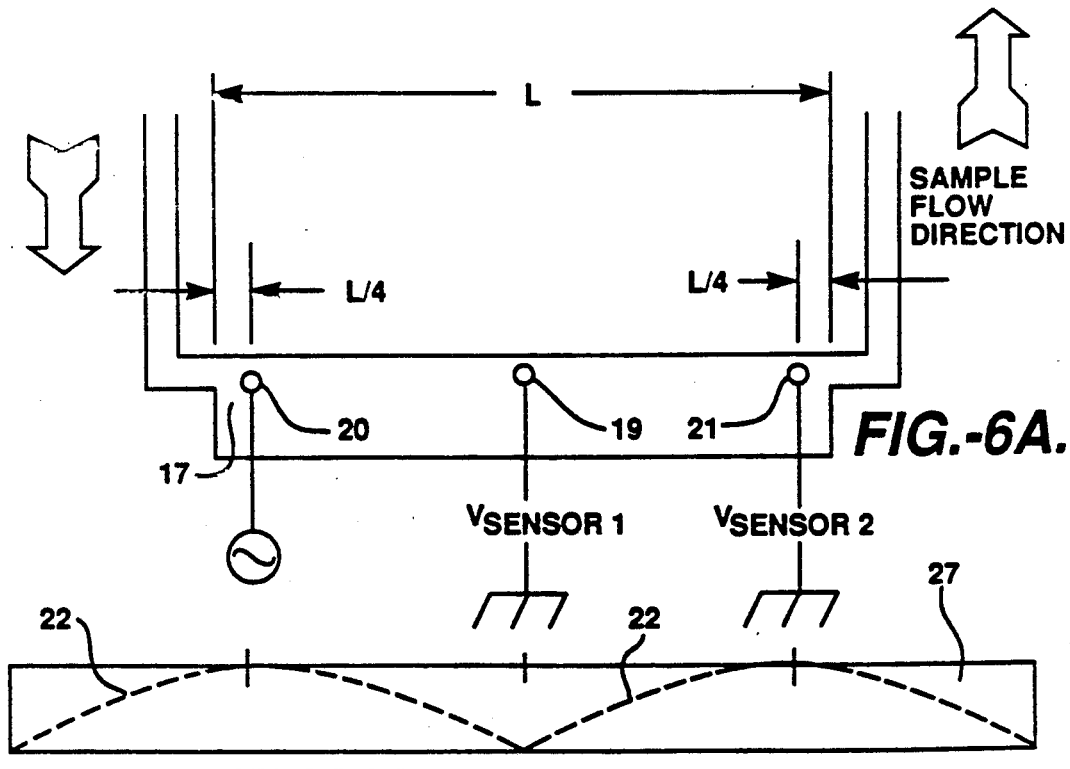
FIG.-6A.
ELECTRIC FIELD
DISTRIBUTION AT 2ND RESONANCE FIG.-6B.

COMPOSITION MONITOR AND MONITORING PROCESS USING IMPEDANCE MEASUREMENTS

FIELD OF THE INVENTION

This invention relates to a system and process for determining the compositional makeup of multicomponent mixtures which are either stationary or flowing in pipes or ducts where the components have different electrical impedance properties and may or may not be present in different states. In particular this invention relates to means and methods for determining the fractional compositional make-up of multicomponent fluids, solids and mixtures thereof whose components have different electrical impedance properties. The fluids, solids and mixtures may be stationary, moving in batches or flowing continuously. More specifically, the invention relates to a system and apparatus which can be used for such things as the continuous and/or stationary composition monitoring of (1) liquids in gases, (2) solids in liquids, and (3) solid, liquid and gas mixtures.

In general the many possible embodiments of this invention, of which some preferred embodiments will be described in this application, furnish economic and practical composition monitoring means that satisfy the needs of a broad range of different industries and laboratories. A characteristic feature of the invention is that its embodiments can, when desirable, be designed and constructed to become integral parts of the processes to be monitored without interfering with the processes. They can be designed and constructed to withstand the processes themselves and the process environments as well as the other process equipment with which they are associated. They can be designed and constructed to be cost effective in terms of acquisition, installation, operation, maintenance, repair and/or replacement. In particular, they can be designed and constructed to be faster and to yield more accurate and wider measurement ranges than present composition monitoring means. They can be designed and constructed to make possible compositional monitoring for a broad range of applications that today are not possible with any monitor.

BACKGROUND OF THE INVENTION

In a host of processes involving solids, liquids, gases and mixtures thereof where the components and mixtures may be stationary, moving in batches or flowing continuously, there are needs for accurate, relatively inexpensive composition monitoring means and methods. Further, it is often desirable that these monitoring means be capable of working in-line with the processes to avoid process detours or by-passes for monitoring reasons. It is often desirable that the monitor be nonintrusive so as not to interfere with the processes being monitored and/or to prevent the monitoring means from being degraded by, for example, processes that are highly corrosive and/or erosive.

Typically such composition monitoring needs are related to the qualities and quantities of products being bought and sold, products being produced or of products being stored. Equally great are the needs for composition monitoring for purposes of process control, production efficiency and safety.

Among the processes having needs for composition monitoring, one particular process is oil production. Whether the oil production is on land or on offshore platforms or on the sea floor there is an unsatisfied need for the continuous monitoring of the quantities of oil, water and gas being produced. There are many different specific reasons for monitoring these three components, but their collective purpose is to optimize production.

Today, the three components of oil, water and gas can only be measured individually by means of separators. For individual well testing, smaller separators with less capacity than production separators are used. These are commonly known as test separators. In a given field, normally only one test separator is available and, therefore, the continuous monitoring of all wells simultaneously is not possible. Instead the wells are only tested at intervals, typically once or twice a month, but longer intervals are not uncommon. Such infrequent and unsatisfactory well testing is also due to the inherent slowness of the separation process and the necessary routine maintenance which includes the removal of deposits, such as sand. In addition there are elaborate and time consuming procedures for routing the production from the individual wells to the test separator.

Therefore, it is clear that there is a specific need for an inexpensive and practical composition monitor that can measure continuously the amounts of oil, water and gas being produced by each individual well in a production field or reservoir in order to know the performance and condition of each well. From these individual measurements, conclusions can be drawn about changes in the reservoir that might affect production rates and total recovery.

Another drawback of test separators is that on offshore platforms they constitute significant structural cost factors. Test separators typically weigh 15 to 20 tons, occupy considerable space and require crews for operation and maintenance. Weight, space and manning are major cost factors on platforms where, for example, the cost penalty per metric ton ranges anywhere from $200,000 to $600,000. Hence, on platforms there is a specific need for replacing the test separators with composition monitors that are light weight and do not require crews for operation. On offshore drilling rigs, an added incentive for replacing the test separators is that their functions are impaired by rig motions (roll and heave) including making them less safe to operate.

For drilling in general there is also a need for a compositional monitor that can measure, continuously, the oil, water, gas and solids content of the returning drilling mud. Among the reasons for such monitoring, the most important is to know if the reservoir is adding fluids to the returning mud and, if so, at what rate. Such reservoir production may signal a possible blow-out that can be prevented with early warning.

The existing means for detecting such influx from the reservoir are primitive and far from adequate. They consist, for example, of liquid level detectors with large tanks that are insensitive to small liquid volume changes.

A very costly composition monitoring task offshore is that of testing the production from subsea wellheads, particularly when the production from several wellheads is commingled into a single flow line to a receiving station. To avoid shutting down all wells but the one to be tested, an additional test line to the receiving station must be employed into which the individual well production is routed for testing at the receiving station. Installing an extra line is costly by itself, but routing of individual well production requires extra equipment, construction and controls that, particularly in a subsea environment, complicate and reduce total production reliability. Clearly, therefore, there is a great economic and practical need for composition monitoring means that can be an integral part of each subsea wellhead such that only the monitoring results need be transmitted to the receiving station by cable or acoustically.

Perhaps the ultimate need for well compositional monitoring means is for installation downhole at the reservoir production zone or zones. No such equipment exists today.

Another need of the petroleum industry for in-line continuous compositional monitoring means is the measurement of small amounts of water in oil for the purpose of custody transfer at points of delivery, at points along the pipeline, at receiving stations and in the further treatment/process and refining of oil products. At present, fiscal measurements are performed by taking frequent small product samples from which, usually by titration processes, the water contents are determined and recorded to give a statistically determined total water content. As can be expected, ignorance about the water content between samples results in disputes about the measurement procedures and the results between sellers and buyers.

In the petroleum industry, reservoir steam injection is often used to enhance and/or make possible the production of heavy oils, i.e. high viscosity oils that cannot flow freely and cannot be pumped. To recover such oils, high energy steam which readily permeates the reservoir is injected into it so that the thermal energy released when the gas condenses will heat the oil to lower its viscosity sufficiently so that it can be produced. During steam injection and after, all reservoir production wells are shut off. After a time, when it is thought that all water vapor has condensed in the reservoir, production begins and is continuous until steam injection is again required. The method here described is usually denoted the "huff and puff" method, but there are also steam "driven" fields where the injection of steam and the production are continuous. Obviously, from the above, it is economically desirable to monitor the quality of the injected steam. The higher the gas content, the higher the quality. Equally obvious is the economic importance of knowing whether or not the produced fluids contain uncondensed steam, which would represent unused energy.

Therefore, the petroleum industry and essentially all steam producers and users have need for continuous steam quality monitoring means. Another example of such producers and users is nuclear power plants.

Outside oil production there are many industries and businesses whose products and processes require close monitoring of composition, but which lack adequate continuous and/or batch monitoring means for doing so.

In the pulp and paper industry, there is a need for continuous monitoring of the water content of pulp liquors being pumped into combustion furnaces. If excessive water is present in the liquor, there is a danger that the furnace will explode. Because of a lack of suitably accurate, noninvasive monitoring means, some pulp and paper companies regularly budget for furnace explosions. An accurate monitoring means could be used to warn of excessively high water content in the liquor.

In the food processing industry, there is a also a need for a monitoring means that could rapidly determine the composition of processed and/or raw foods. Of particular concern is the water content. The dairy industry is a typical example. The fat and water content of milk and milk products must meet certain specifications to be sold in the marketplace, yet no adequate monitoring means for continuously measuring the fat and water content has been found. Consequently, dairy producers must put excessive milk fat into their products to ensure that they meet specifications. If an accurate, simple, continuous fat and water content monitoring means were available, the extra milk fat could be put towards the production of butter or ice cream.

Fuel transportation and distribution systems have need for an accurate, continuous means for monitoring the water content of the fuels. For example, there is a need to measure the water content of jet fuels when they are being pumped into aircraft. A small percentage of water is added to jet fuels to improve combustion efficiency, but if excessive water is present, serious problems can occur during operation, including engine failure.

Within the petrochemical and chemical industries, there are a host of composition monitoring needs where the liquids involved may not be water. Examples of such process liquids are plastic resins, polymers, alcohols, acids, and organic solvents. In each case, there exists a need for a simple, continuous, rugged, chemically inert, and inexpensive monitoring means which can continuously measure the composition of mixtures of these chemicals as they are being processed and purified.

For many of the composition monitoring examples cited, no technology is currently available to perform the process monitoring tasks. It is an object of this invention to describe a monitoring means and apparatus which satisfies the central composition monitoring requirements that are common to these and many other applications like them. The common requirements are that a monitoring means be:

1) in-line,
2) measure continuously (i.e. have a short measurement cycle time),
3) able to withstand
Difficult process conditions,
High internal temperatures and pressures
Corrosive process components
Abrasive components
Viscous liquids,
4) noninvasive,
5) accurate,
6) insensitive to geometry outside test section
7) reliable,
8) relatively inexpensive,
9) and tough enough to withstand industrial environments.

DESCRIPTION OF THE PRIOR ART

The concept of using a process stream pipe as a waveguide for making RF dielectric measurements of the process stream is not a new one. Other apparatus described in the patent literature which describe RF permittivity waveguide measurements made in pipes differ in their function considerably. Most are amplitude measurement systems for which accuracies of even one part in a thousand would be difficult to maintain over time. Examples of such systems are disclosed in U.S. Pat. No. 4,651,085, issued July 10, 1984 to Sakurai et al.; U.S. Pat. No. 3,498,112, issued Mar. 3, 1970 to Howard; U.S.

Pat. No. 3,883,798, issued May 13, 1975 to Free; and U.S. Pat. No. 4,301,400, issued Nov. 17, 1981 to Paap. Some measure phase, such as U.S. Pat. No. 4,423,623, issued Jan. 3, 1984 to Ho et al. Here too, accuracy of better than one part in a thousand over time would be difficult. The Ho et al. patent claims to measure the cutoff frequency of a waveguide which fundamentally is an amplitude measurement as a function of frequency; however, defining the cutoff frequency is somewhat arbitrary and not possible to measure directly. At heart the apparatus described in the Ho et al. patent utilizes either amplitude or phase measurements and so too is not capable of the precision of a true frequency discriminating device. The device in the Free et al. patent measures frequency, but is not well adapted for measuring composition of materials over a wide range with large variations in permittivity. That device isolates its test section by providing a different field orientation at each end of the test section. While such a field orientation difference is easily provided with a rectangular cross-section waveguide, it cannot be provided with a circular cross-section waveguide. In order to provide a central continuous feed path in the Free et al. device, slabs of a material having a permittivity similar to that of the material being measured in the device are provided in the terminations on each end of the test section. The device is less sensitive the greater the variation between the permittivity of the slab and the permittivity of the material being measured.

A variety of other monitor systems for fluids are known in the prior art. Meador et al., U.S. Pat. No. 4,458,524, issued July 10, 1984, discloses a crude oil production stream analyzer which utilizes dielectric constant, density and temperature measurements to determine composition of the crude oil production stream. That device also relies on phase shifts to determine the dielectric constant. Other composition monitors are disclosed in the following additional issued U.S. Pat. Nos.: 3,688,188, issued Aug. 29, 1972 to Bak et al.; U.S. Pat. No. 3,816,811, issued June 11, 1974 to Cmelik K.; U.S. Pat. No. 3,826,978, issued July 30, 1974 to Kelly; U.S. Pat. No. 3,889,182, issued June 10, 1975 to Easley et al.; U.S. Pat. No. 3,897,798, issued Aug. 5, 1975 to De Vale; U.S. Pat. No. 4,104,585, issued Aug. 1, 1978 to Schofield; U.S. Pat. No. 4,124,475, issued Nov. 7, 1978 to Zetter et al.; U.S. Pat. No. 4,266,188, issued May 5, 1981 to Thompson; U.S. Pat. No. 4,288,741, issued Sept. 8, 1981 to Dechene et al.; U.S. Pat. No. 4,327,323, issued Apr. 27, 1982 to Walker; U.S. Pat. No. 4,340,938, issued July 20, 1982 to Rosso; U.S. Pat. No. 4,345,204, issued Aug. 17, 1982 to Shelley; U.S. Pat. No. 4,370,611, issued Jan. 25, 1983 to Gregory et al; U.S. Pat. No. 4,387,165, issued June 7, 1983 to Youngblood; U.S. Pat. No. 4,429,273, issued Jan. 31, 1984 to Mazzagatti; U.S. Pat. No. 4,441,362, issued Apr. 10, 1984 to Carlson; U.S. Pat. No. 4,543,191, issued Sept. 24, 1985 to Stewart et al.; U.S. Pat. No. 4,555,661, issued Nov. 26, 1985 to Benson et al.; U.S. Pat. No. 4,559,493, issued Dec. 17, 1985 to Goldberg et al. However, none of these systems are capable of monitoring a multiple component fluid flowing in a pipe without interfering with the fluid flow or without subjecting system components to damage by the fluid.

Capacitance meters and conductivity meters have commonly been used in the past for the purpose of monitoring the composition of liquid process streams. For example, capacitance meters are disclosed in U.S. Pat. No. 4,266,425, issued May 12, 1981 to Allport and Scott et al., published European Patent Application 0268399, dated May 25, 1988. The RF impedance monitoring methods described in this specification have several fundamental advantages over these lower frequency methods. Lower frequency devices are more flow sensitive and more sensitive to salt content in the water. Capacitance meters do not function accurately when water is the continuous phase of an mixture unless the conductivity of the water is low. It is also very difficult to design a single measurement unit capable of measuring the permittivity and the conductivity of process streams having impedance properties like those of oil/water mixtures. The reason for this is that the relative impedance levels of the oil continuous mixtures and the water continuous ones are different by many orders of magnitude. Finally, the potential accuracy of the capacitance meter is not much better than one part in a thousand for long term usage because the capacitances being measured are so small—full scale is just tens of picofarads. Stability is hard to achieve because of signal line capacitance drifts, temperature drifts, signal drifts, etc. From a mechanical standpoint, many capacitance meters use coaxial electrodes, one of which is centered in the middle of the pipe. In such a configuration, they make it impossible to clean out the pipe with standard techniques. In addition, they are exposed to the corrosive and abrasive environment of many process streams.

It is further known in the art to use cross correlation techniques to determine flow rate from measurements taken at different points along a vessel through which a fluid flows. Such flow rate devices are disclosed in, for example, U.S. Pat. Nos. 3,762,221, issued Oct. 2, 1973 to Coulthard; U.S. Pat. No. 3,967,500, issued July 6, 1976 to Forster; U.S. Pat. No. 4,248,085, issued Feb. 3, 1981 to Coulthard; U.S. Pat. No. 4,257,275, issued Mar. 24, 1981 to Kurita et al.; U.S. Pat. No. 4,380,924, issued Apr. 26, 1983 to Nakamoto et al.; U.S. Pat. No. 4,402,230, issued Sept. 6, 1983 to Raptis; U.S. Pat. No. 4,417,584, issued Nov. 29, 1983 to Cathignol et al; the above-referenced U.S. Pat. No. 4,423,623; U.S. Pat. No. 4,693,319, issued Sept. 15, 1987 to Amemiya and U.S. Pat. No. 4,708,021, issued Nov. 24, 1987 to Braun et al. However, all of these devices obtain the measurements that are cross correlated in a different way than in this invention. U.S. Pat. No. 4,548,506, issued Oct. 22, 1985 cross correlates signals based on dielectric properties of a material, but not for determining flow rate.

SUMMARY OF THE INVENTION

Accordingly, it is an object of this invention to provide a novel multicomponent fluid monitor and monitoring process which will monitor the composition of such a multicomponent fluid flowing in a pipe without significantly interfering with the fluid flow.

It is another object of the invention to provide such a monitor and process in which active electrical components of the monitor need not be in physical contact with the fluid.

It is still another object of the invention to provide such a monitor and process which is capable of monitoring the composition of a multicomponent fluid having a broader range of dielectric properties than is possible with prior art monitors and processes.

It is a still further object of the invention to provide such a monitor and process which is capable of monitoring the composition of a multicomponent fluid having a higher conductivity than is possible with prior art monitors and processes.

It is a further object of the invention to provide such a monitor and process which is capable of monitoring such a fluid composition when one of the components of the mixture is salt water.

It is still another object of the invention to provide such a monitor and process in which a standing electromagnetic wave pattern is generated, thus simplifying the transduction mechanism and improving accuracy.

It is yet another object of the invention to provide such a monitor and process which are capable of determining whether the fluid being monitored is evenly mixed.

It is another object of the invention to provide such a monitor and process in which the composition of a three component flow is determined on the basis of dielectric constant and/or conductivity and density measurements.

It is still another object of the invention to provide a highly accurate, frequency discriminated two-component fluid flow monitor.

It is another object of the invention to provide a system incorporating such a monitor and process which is capable of measuring flow rate of a fluid, the composition of which is being monitored with the monitor and process.

This invention describes a monitoring method and apparatus capable of addressing composition monitoring needs of this kind. In addition, this device can be used to monitor mixtures where multiple flow regimes are possible due to the immiscibility of the mixture components. Finally, the device is designed for simple manufacture and relatively low cost to the user.

The apparatus works by measuring either the radio frequency permittivity and/or conductivity of the process stream of interest. When more than two components are present, a density measurement can be combined with the RF impedance measurement. For most applications, the operating frequencies of the apparatus are between 50 MHz and 3 GHz. When necessary, the apparatus also uses temperature and pressure information to correct component impedance calibration data.

This invention utilizes radio frequency (RF) bridge techniques to parameterize the complex dielectric properties of materials in an electrically isolated, physically open structure. The primary RF parameters, used to characterize the material under test, are frequency and attenuation. The device functions by using the metal pipe of the process stream as an electromagnetic waveguide. Electromagnetic energy of the appropriate frequency is coupled through apertures cut into the pipe. This energy is measured at some distance down the guide through another aperture. From this measurement is derived the impedance properties of the mixture. Mixture temperature and pressure data from monitors are used to make corrections for varying component impedance properties. The mixture impedance data is used in turn to determine the composition of the stream using either calibration curves or a theoretical composition vs. dielectric model. Advantages of the aperture coupled waveguide concept are that it makes fabrication of the device relatively simple, and it makes possible a noninvasive, in-line process monitor. No antennae or electrodes intrude into the fluid flow cross-section inside the pipe.

An additional characteristic of the method and apparatus of this invention is that they can be used to determine when the process stream is evenly mixed. This capability is important because many of the applications for which the device would be of greatest utility concern measurement of immiscible components in the stream. Relating the measured impedance properties to the composition of the mixture depends on the fluid being in a known flow regime.

A novel feature of the concept described herein is the means by which the measurement is made. The device is constructed in such a way that within a test measurement region of a known length, propagating electromagnetic waves traveling in opposite directions in the pipe are caused to interfere. At certain characteristic operating frequencies the interference is entirely constructive or destructive. It is a simple matter to relate these characteristic frequencies to the permittivity of the process stream in the pipe. Thus, in operation, the apparatus of this invention functions by sweeping the operating frequency of the input aperture or apertures and measures the insertion loss via receiving apertures located elsewhere in the test section. When the insertion loss reaches a maximum or a minimum the operating frequency is recorded and the fluid permittivity is thereby inferred. The device can be constructed in several different ways. Several methods will be described in this specification. It is the technique in general, however, which is the subject of this invention.

In a well designed apparatus utilizing the interference section concept, the characteristic frequencies are very sharply defined; hence, tremendous accuracy is possible in determining the characteristic frequencies. It is possible to identify them to better than one part in $10^5$ (10 kHz in 1 GHz). Instrumentation is readily available for generating and measuring frequencies to this precision. It is because of these fundamental characteristics that the method and apparatus of this invention can be used for such applications as steam quality monitoring and fiscal monitoring of pipeline quality oil. These applications require permittivity accuracy to about 1 part in 10000 or better.

The attainment of the above and related objects may be achieved through use of the novel multicomponent monitor and process herein disclosed. In one aspect of the invention, a fluid monitor in accordance with the invention includes a means for creating an electromagnetic interference in a test section built into a section of pipe or other fluid confining structure in which the measurements are taken. At characteristic frequencies the interference is constructive or destructive. The characteristic frequency can be related simply to the permittivity of the process stream. Such a measurement method substantially simplifies the transduction means and improves accuracy. In another aspect of the invention, several transmission and receiving aperture pairs in the measurement section are used to determine whether the fluid in the pipe is evenly mixed. Even mixing is essential for accurate fluid composition monitoring. In a third aspect of the invention, the composition of a fluid flow stream consisting of at least three components is determined by the monitor and process on the basis of dielectric constant or conductivity and density measurements.

A multicomponent composition monitor transducer in accordance with the invention has an electrically conductive wall enclosing the composition. One or more electromagnetic wave transmitting apertures and an electromagnetic wave receiving aperture face the enclosure. The transmitting apertures are positioned to create electromagnetic waves in the enclosure and the receiving aperture is positioned to receive electromagnetic waves from the enclosure. A means for inducing an electromagnetic interference pattern in a test section including the transmitting aperture(s) and the receiving aperture is positioned between two parallel planes extending across the test section. In another aspect of the invention, the fluid flow composition monitor includes a means for electrically isolating the test section.

The attainment of the foregoing and related objects, advantages and features of the invention should be more readily apparent to those skilled in the art, after reviewing the following more detailed description of the invention together with the drawings, in which:

BRIEF DESCRIPTION OF THE DRAWINGS

FIG. 4 is a schematic representation of a second generalized composition monitor in accordance with the invention.

FIG. 5 is a schematic representation of a third generalized composition monitor in accordance with the invention.

FIG. 6a is a schematic cross section view of a fourth generalized composition monitor in accordance with the invention.

FIG. 6b is a cross section view of a portion of the generalized composition monitor shown in FIG. 6a.

THEORETICAL BACKGROUND OF THE INVENTION

Figure 1:
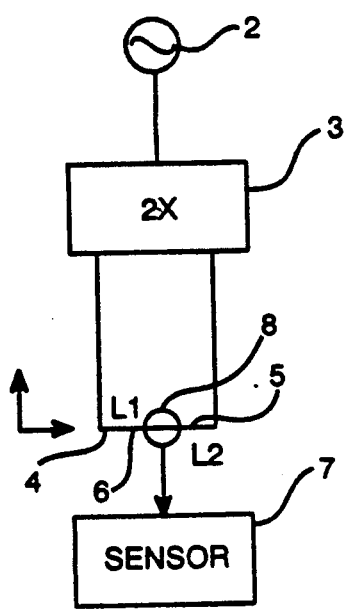
FIG. 1 is a schematic, generalized representation of a composition monitor in accordance with the invention.

The use of frequency and attenuation parameters and the theoretical basis for this invention will be explained using the transmission-line model shown in FIG. 1. In this figure, a sinusoidal RF signal from source 2 is split into two equal, in phase signals at 3 which drive both ends 4 and 5 of a transmission line 6. A voltage sensor 7 is coupled to this transmission line at a point 8 which is not equidistant from the two ends 4 and 5. Assuming, for the sake of this illustration, that the voltage sensor 7 is loosely coupled to the transmission line 6 and that the transmission line is well matched at both ends, one can express the voltage at the sensor 7 as the sum of two vectors:

$$Vp = Vo[exp(G*L1) + exp(--G*L2)] \quad (1)$$

where, for the lossless case, the complex propagation constant (G) is imaginary, and L1, L2 represent the physical lengths between the ends 4 and 5 of the transmission line and the voltage sensor 7. The negative sign in the second term is due to the choice of coordinate system. In this case we have taken the origin of our coordinate system to be to the left of the figure. This results in L1 being positive and L2 being negative. Hence, in both terms, the amplitude of the voltage is smaller than, and its phase is lagging, that of the respective driving point. The complex propagation constant depends on the geometry of the transmission line 6 and on its constituent materials. For example, if we construct a hollow transmission line and fill it with deionized water then this composite transmission line will have specific propagation constant and produce a specific sensor voltage (a specific amplitude and phase). If we add some salt to the water in the transmission line then the propagation constant will change and so will the sensor voltage. Since the salt introduces ions to the solution, its conductivity changes, which shows up primarily as a change in the real part of the propagation constant. At the sensor 7, the addition of salt produces a change in amplitude while the phase remains essentially unchanged.

There are several ways to improve the above system's sensitivity to these changes. We will discuss several such methods, realizing that those versed in the art can use other methods to realize the present invention. The first method utilizes a generalized resistance-ratio bridge 9 such as that shown in FIG. 2. In this case the reference setting of the test cell (a hollow transmission line, L1 in the example) is established by adjusting the attenuator (RT) and the phase shifter ($\phi$T) until the sensor voltage is null. Then any change in the test cell's impedance and/or propagation characteristics will unbalance the bridge 9. The sensitivity of the bridge 9, in this case, is adjustable by changing the ratio of the fixed arm impedances (R1 and R2).

Figure 3:
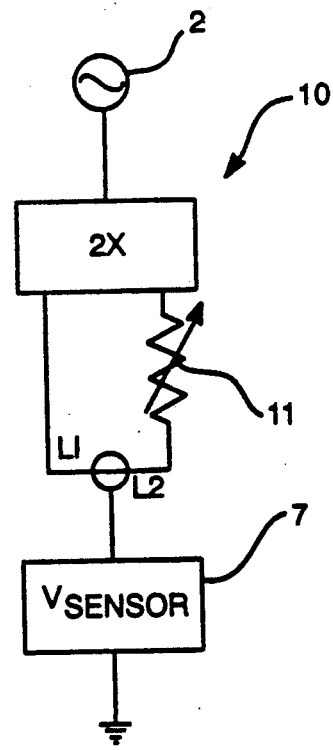
FIG. 3 is a schematic diagram of another circuit used to increase sensitivity of the FIG. 1 generalized composition monitor.

The second method uses the setup 10 shown in FIG. 3 and generates the reference null by either adjusting the difference between the transmission line lengths (L1 and L2) or by adjusting the frequency of the RF source 2. In either case, the objective is to obtain a transmission phase shift difference between the two parts of the test cell (L1 and L2) of 180 degrees. When a lossy material fills the test cell, the amplitudes of the two waves at the sensor will not be equal and consequently will not cancel one another to produce the null. One then adjusts the attenuator 11 shown in the figure to obtain the desired null at the sensor 7. Another, less sensitive, variation on this technique consists of using arbitrary lengths in the test cell, inserting a phase shifter in series with the attenuator and use it (instead of frequency) to set the transmission phase shift difference as described above.

The preceding discussion assumed that the transmission line was well matched outside of the test cell. This allows one to ignore any reflections due to mismatches outside of the test cell. In practice, this can be accomplished by putting resistive or reactive terminating sections on both ends of the test cell. The use of resistive terminations 12 and 13 as shown in FIG. 4 will be discussed first. In this figure, the RF energy is coupled into the test cell at points A and B. The sensor voltage is coupled out at point C and the remaining energy is absorbed by the well matched terminations 12 and 13 on either end (marked T). If we continue the example of a hollow transmission line such as a pipe, these terminations 12 and 13 isolate the test cell from the rest of the piping system. In other words bends and/or valves in the pipe outside of these terminations 12 and 13 will have little or no effect on the sensor 7 output.

In order for reactive terminating sections to isolate the test cell from the rest of the piping system, the magnitude of the terminating sections reactance must either be very large or very small. Ideally the magnitude of the reflection coefficient, at the interface between the test cell and the reactive terminating section, would be unity. When the test cell is filled with a lossless material, the test signal is reflected back and forth by these terminations. As a result, one of the signal input ports represented by A and B in FIG. 4 can be deleted. One could also delete the sensor 7 at point C and insert a directional coupler in the remaining input line. The signal reflected by the test cell as monitored by this directional coupler would then be the sensor signal. This test setup variant is useful for monitoring the composition of low-loss materials but lacks sensitivity as the dissipation factor of the test materials increases.

A test setup 14 using a test cell with reactive terminations 15 and 16 and improved sensitivity for monitoring the composition of lossy materials is shown in FIG. 5. In this realization, the relation given in equation 1 still applies but now the reverse traveling wave is produced by the reflection at the reactive termination 15 or 16. It is evident to those versed in the art that this type of test cell, like those described earlier, can be realized in several ways. The reactive terminations 15 and 16 can be produced by using cutoff waveguide, bandreject structures or other coupling elements. The locations of the source 2 and sensor 7 (A and B in the figure) are variable depending on the operating characteristic desired. The source and sensor coupling elements need not be of the same geometry or type. One could utilize electric-field coupling while the other utilized magnetic-field coupling.

As a simple example of such a test cell, consider a rectangular waveguide 17 of length (L), called the test section, terminated at both ends with similar waveguides 18 whose width is half that of the test section as shown in FIG. 6a. For this example, the length of the test section is between 3 and 4 times its width. Three E-field probes 19, 20 and 21 are assumed, one 19 centered along the length of this section and other two 20 and 21 somewhat less than a quarter of this length from each end of the test section 17 as shown in the figure. If a low-loss sample fluid is allowed to flow through this waveguide structure and the frequency of the test oscillator 20 is adjusted to the second cavity resonance, the magnitude of the electric-field 22 in the test section will be as shown in FIG. 6b. This field distribution is strongly coupled to the test frequency source 20 and the probe 21 associated with sensor #2 but a reference null is produced at the probe 19 associated with sensor #1. As discussed earlier, this null is a sensitive indicator for any change in the sample's dielectric properties.

This invention exploits the dependence between the complex propagation constant and the complex dielectric constant of the material comprising the transmission line to realize a very sensitive process monitor.

In the analysis of a particular transmission structure, such as waveguide or coax, containing a prescribed material such as air or some other material, one begins with Maxwell's equations and the constitutive equations for the medium. The constitutive equation of interest here is the relation between electric flux density (D) and the electric field (E) in the medium.

$$\vec{D} := \epsilon \vec{E}$$

This fundamental relationship incorporates the material properties into the equations for propagation at the outset. The permittivity ($\epsilon$) is a scalar for isotropic materials and a tensor for anisotropic materials. For our present discussion, we will assume an isotropic material, $\epsilon$ a scalar. The form of the resultant propagation equation depends on the modes supported by the structure. For transverse electromagnetic (TEM) waves the propagation equation is $$\Gamma^2 + K^2 := 0$$

where $\Gamma$ represents the propagation constant and K is given by:

$$K^2 := \omega^2 \mu \epsilon$$

In the TEM case, the propagation constant is proportional to the square root of the dielectric constant.

For transverse electric (TE) or transverse magnetic (TM) waves the propagation equation is $$\Gamma^2 := Kc^2 - K^2$$

where Kc is a constant determined by the mode and the boundary conditions of interest. These relations can be used to determine the material's permittivity from measurements of the propagation constant.

DETAILED DESCRIPTION OF THE INVENTION

The method and apparatus of this invention concerns a technique for performing radio frequency dielectric measurements of materials. This information can be used to determine the composition of the material, the homogeneity of the material, and/or the material's rate of flow if it is moving in some manner.

The apparatus of this invention has a unique structure which is electrically isolated but physically open. The electrical isolation of the test section is accomplished in a manner which makes possible very accurate dielectric measurements of the materials being measured. The physically open structure makes it possible to measure continuously flowing materials, to measure materials in batches, or simply to measure single units of material that are inserted in the test section. Structurally, the test section is a hollow transmission line through which electromagnetic waves can propagate in the manner of a waveguide and into which the material of interest is introduced. Electrodes, antennas, or other apparatus need not protrude into the test section. The apparatus of the invention can be constructed to withstand high internal temperatures and pressures in the test section. The materials to be measured can be very corrosive or abrasive without significantly damaging the monitoring apparatus or diminishing its performance over time. In general, the apparatus of this invention is appropriate for monitoring the composition of materials in a host of difficult industrial process settings.

Figure 7:
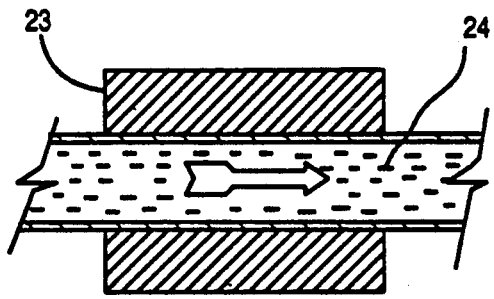
FIGS. 7-11 are schematic cross-section views of generalized composition monitors in accordance with the invention, showing different uses for them.

The method and apparatus of this invention are generally useful for the measurement of a wide range of different materials where the material's dielectric properties can be related to composition. The method and apparatus can be used to measure liquids, solids, gases and mixtures thereof. For example:

1) The method and apparatus of this invention can be used to measure the composition, flow rate, and/or homogeneity of liquids or liquid mixtures. Applications include the continuous compositional determination of oil/water mixtures or the determination of the degree of polymerization of a batch of plastic resin. FIG. 7 illustrates how apparatus 23 would be used to measure a liquid 24.

Figure 8:
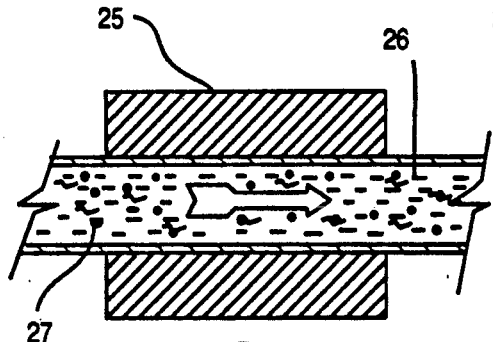

2) The method and apparatus of this invention can be used to determine the composition, flow rate, or homogeneity of solid and liquid mixtures. Applications include the measurement of the coal content of coal slurries, the fat content of milk, or the sewage content of waste water. FIG. 8 illustrates how apparatus 25 would be used to measure liquid 26 (dashed lines) and solid 27 mixtures.

Figure 9:
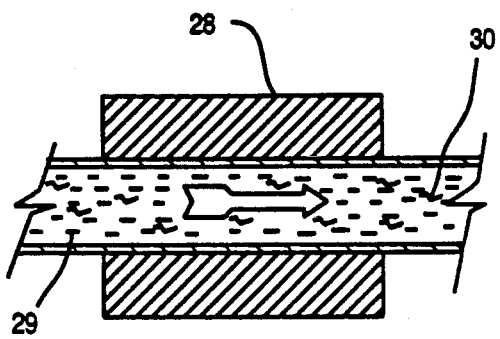

3) The method and apparatus of this invention can be used to determine the composition, flow rate, and homogeneity of liquid and gas mixtures. Applications include monitoring the void content of saturated steam which can be used to help determine steam quality or measuring oil, water, and gas mixtures flowing from oil wells. FIG. 9 illustrates how apparatus 28 would be used to measure liquid 29 (dashed lines) and gas 30 (wavy lines) mixtures.

Figure 10:
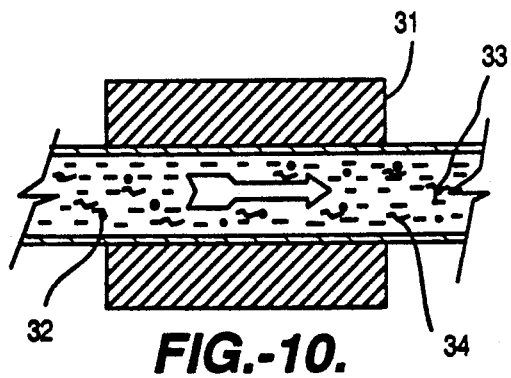

4) The method and apparatus of this invention can be used to determine the composition, flow rate, and homogeneity of solid, liquid, and gas mixtures. Applications include monitoring the water and gas content of drilling mud in the oil industry or measuring the water content of drying food. FIG. 10 illustrates how apparatus 31 would be used to measure solid 32, liquid 33, and gas 34 mixtures.

Figure 11:
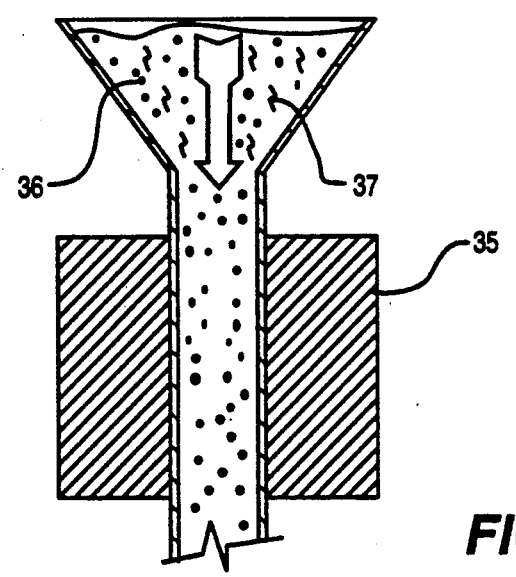

5) The method and apparatus of this invention can be used to determine the composition, flow rate, and homogeneity of mixtures of solids and gases. One application is monitoring the solids content of powders. FIG. 11 illustrates how apparatus 35 would be used to measure solid 36 and gas 37 mixtures.

Even when the composition of the measured material or mixture cannot be determined in closed form by the dielectric information provided by the method and apparatus of this invention, the apparatus can nevertheless be used as an accurate trend monitor.

The method and apparatus of this invention functions by exciting electromagnetic wave propagation in a hollow metal test section that acts as a waveguide. The electromagnetic energy is coupled into the waveguide structure through dielectrically loaded apertures cut into the metal waveguide. In essence, the waveguide test section is a specially designed section of pipe. The test section is terminated at the ends in order to electrically isolate the test section from other equipment located nearby. The terminations take the form of either reactive or resistive loads.

The apparatus of this invention is designed to cause electromagnetic energy propagating in opposite directions in the waveguide test section to interfere. By sweeping the operating frequency, those frequencies at which constructive or destructive interference occur can be identified. This information can be related to material dielectric properties which, in turn, can be related to material compositional information.

The apparatus operates as an RF balanced bridge where signals in two different propagation arms are balanced in phase and magnitude in order to produce a sharp peak or null. The frequency at which the peak or null occurs can be measured with great precision. This novel scheme for measuring material dielectric properties in a physically open structure makes possible continuous RF permittivity measurements of materials to an accuracy heretofore unrealizable in industrially useful devices.

When the conductivity of the test material is high, the attenuation of the propagating electromagnetic energy in the waveguide test section becomes significant. If the conductivity is high enough, the interference pattern is not discernable and the permittivity cannot be determined with the technique shown in FIG. 3. Instead the apparatus will measure the attenuation of the electromagnetic energy between the coupling slots at certain fixed frequencies. From these measurements, the conductivity of the test material will be determined.

The novel apparatus of this invention for obtaining RF dielectric information about materials improves on two important limitations inherent in prior art techniques for monitoring the composition of industrial process streams based on RF measurements.

First, it simplifies the transduction of measured electromagnetic amplitude and phase measurements into accurate process stream dielectric information. The characteristic frequencies at which constructive or destructive interference occur for a given process fluid depend almost entirely on only five parameters: the length of the test section, the diameter of the pipe inside the test section, the reflection coefficient of the terminating sections, the spacing between the various coupling slots, and the permittivity of the fluid. When the source is weakly coupled to the test section, the external signal generating circuit has very little effect on the balanced bridge measurement. More importantly, the coupling mechanism between the signal source and the test section needn't be well characterized. Hence, a relatively simple relationship exists between the measured characteristic frequencies and material permittivity. This simplicity results directly in improved accuracy. It also makes it much less difficult to apply the apparatus to a wide variety of different materials with widely varying dielectric properties without the need for significant redesigning.

The second fundamental advantage of this invention derives from its insensitivity to measurement perturbations caused by process equipment external to the test section. In an industrial setting, a composition monitoring apparatus of the type described herein could be placed anywhere in a process pipeline. It could be placed several feet beyond a pump, adjacent to an invasive flow meter, a valve, or simply adjacent to a bend in the pipe. When the process material is relatively lossless in an electrical sense, these objects would reflect spurious energy back into the test section of a waveguide based composition monitor. This reflected energy would modify the amplitude and phase characteristics of the measured signal, thus degrading the accuracy of the device. The method and apparatus of this invention electrically isolates the test section of the device from the rest of the installation such that virtually no electromagnetic energy propagates beyond the test section. This eliminates the possibility of measurement error caused by the reflection of spurious energy at a pipe discontinuity back into the test section. It also makes it possible to use the apparatus of this invention as a stand alone material composition monitor which is not even connected into a pipeline.

The novel apparatus of this invention deduces changes in material composition, flow rate, and/or homogeneity on the basis of measured material RF dielectric properties. The dielectric properties of many materials vary as a function of temperature and pressure. In order to make corrections for such variations, the apparatus of this invention includes temperature and pressure measuring devices when necessary.

Many physical embodiments of this method are possible which structurally induce electromagnetic interference patterns in a physically open, but electrically isolated waveguide test section. Several embodiments will be described here in detail. However, many other embodiments of the method taught by this invention are possible. Different coupling mechanisms, aperture structures, waveguide modes, termination methods, aperture positions, waveguide structures (rectangular instead of circular for example), etc. could be used without deviating from the monitor and process of this invention.

GENERAL BALANCED BRIDGE EMBODIMENTS

The general balanced bridge method of measurement consists of a method whereby two identical electrical signals are passed through differing electrical paths, or arms, for which the dielectric properties of one of the arms is to be determined. The transmission properties of the other are adjusted at a fixed frequency until the two output signals balance, or cancel, and produce a null. The transmission properties (amplitude and phase) at which the balancing arm are set when the null is achieved are uniquely related to the transmission properties in the unknown arm of the bridge. This is the method illustrated by FIG. 2.

In those cases where the versatility of the full balanced bridge is not required one can use the approach described earlier and shown in FIG. 4. In this case, the dielectric properties of each arm are the same, but unknown. The imbalance in the two arms is achieved by making the electrical lengths of each different. In order to balance the arms of the bridge, the phase and amplitude of the two signals is adjusted until a null is produced at the output. This is accomplished by varying the frequency of both input signals and the amplitude of one of them until a null appears at the output. This is the mode of operation illustrated in FIG. 3. The dielectric properties of the test material can then be determined from the frequency or frequencies at which the null occurs, the difference in electrical lengths of the two bridge arms, and the attenuation applied to one signal to produce the null on the output. The mode of operation will be described in more detail in the description of Embodiment 1.

Figure 12:
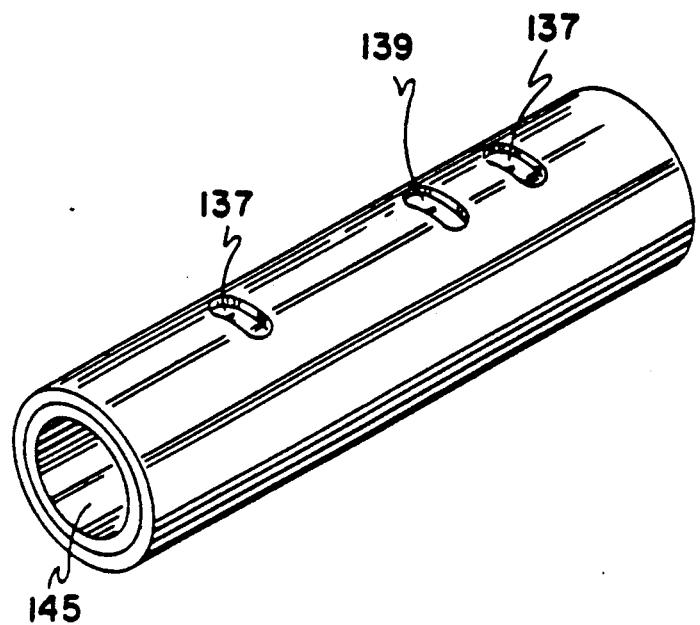
FIG. 12 is a perspective view of a first embodiment of a monitor in accordance with the invention.
Figure 13:
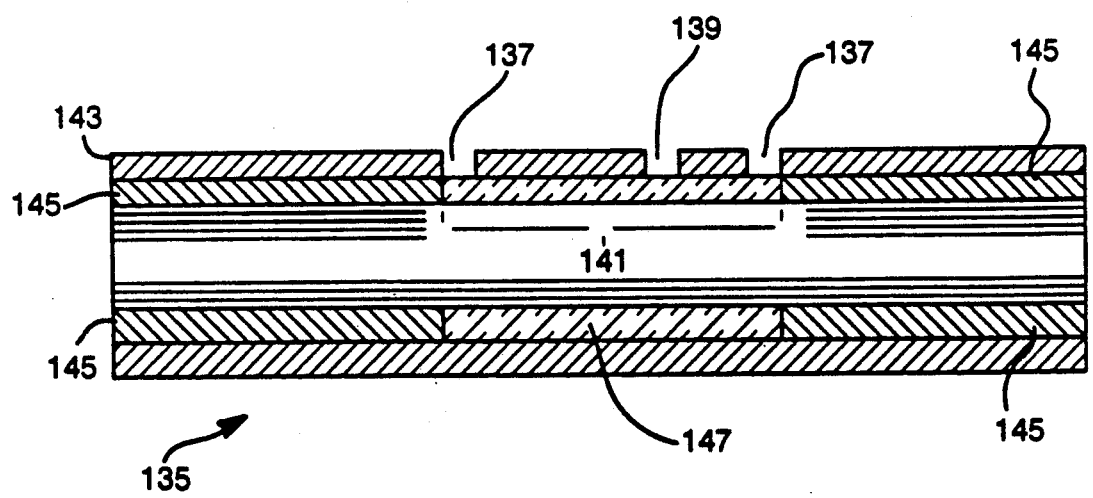
FIG. 13 is a cross-section view, taken along the line 13-13 in FIG. 12.
Figure 14:
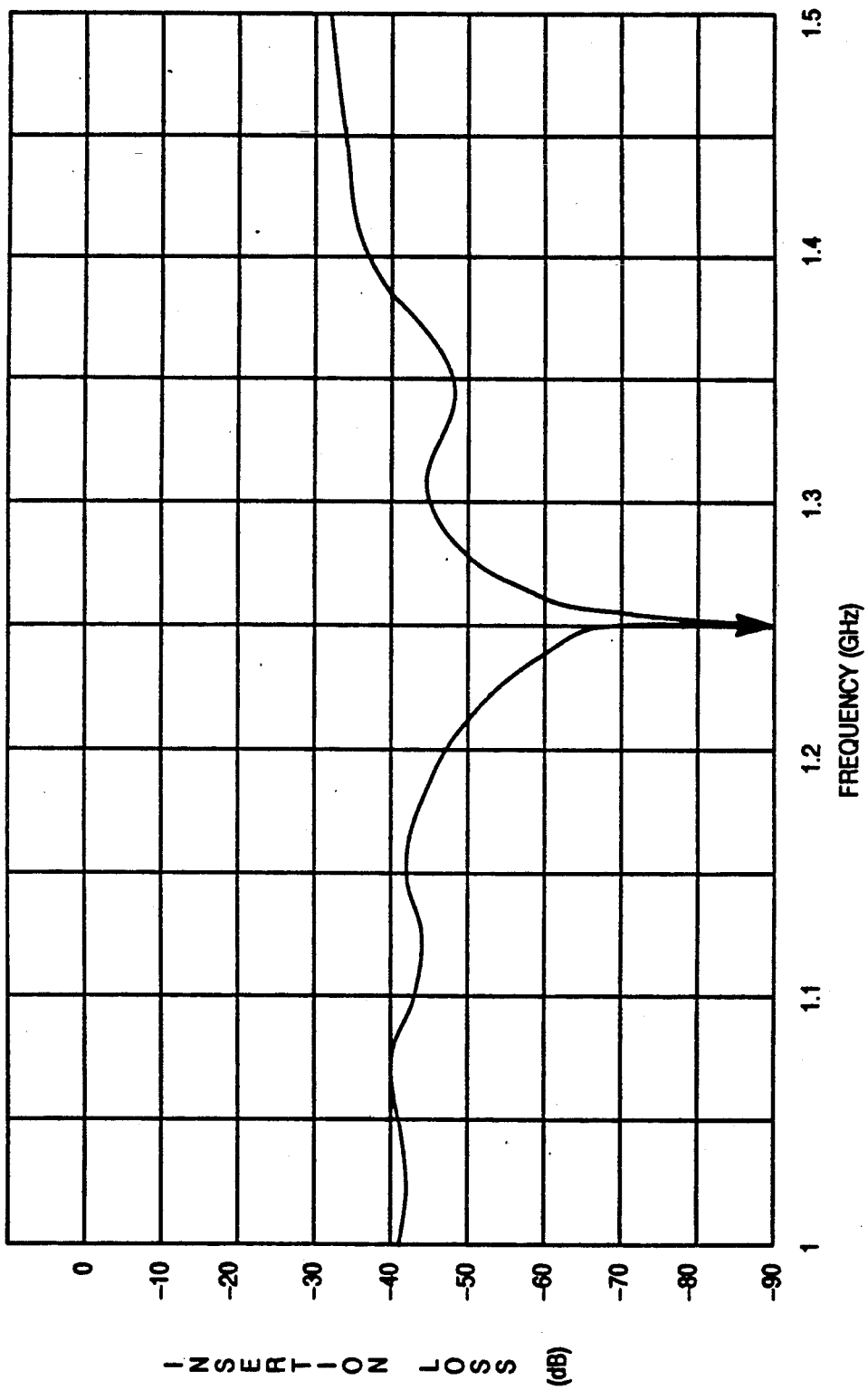
FIG. 14 is a graph of experimental results obtained with a monitor in accordance with the invention.

Embodiment 1—The first embodiment of this invention implementing the concept shown in FIG. 4 is shown in FIG. 12 and 13. It uses two transmission apertures 137 to introduce two propagating waves of the same frequency into the waveguide. One receiving aperture 139 is placed asymmetrically between the transmission apertures 137 to sample the interference waveform that results. The test section 141 is terminated with resistive loads 145 to absorb the electromagnetic energy which escapes the test section. At certain fixed frequencies, the phase difference between the two waves at the receiving aperture is an integral multiple of 180°, i.e. the electrical length difference is an integral multiple of one half the wavelength. At these frequencies, the insertion loss measured at the receiving aperture 139 is simply the difference in the amplitude of the two waves. If the amplitudes of both two waves are equal at the receiving aperture, then a sharp null appears in the measured insertion loss spectrum. The amplitude balance is made by adjusting the attenuation of the input signal going into the transmitting aperture closest to the receiving aperture. FIG. 14 shows the insertion loss spectrum of a prototype of this embodiment.

The two test section lengths between the transmitting apertures and the receiving aperture represent the two arms of the bridge measurement apparatus. When the measured signals are 180° out of phase and balanced in magnitude, a null appears at the output. The characteristic frequencies, the difference in electrical lengths of the two signal paths, and the difference in attenuation of the two signal paths can be related directly to the permittivity and conductivity of the material in the test section. Even when the measured material is so conductive as to prevent adequate resolution of a null, the conductivity of the process stream can be determined by simply measuring the attenuation in signal in the shortest arm of the test section bridge.

Figure 15:
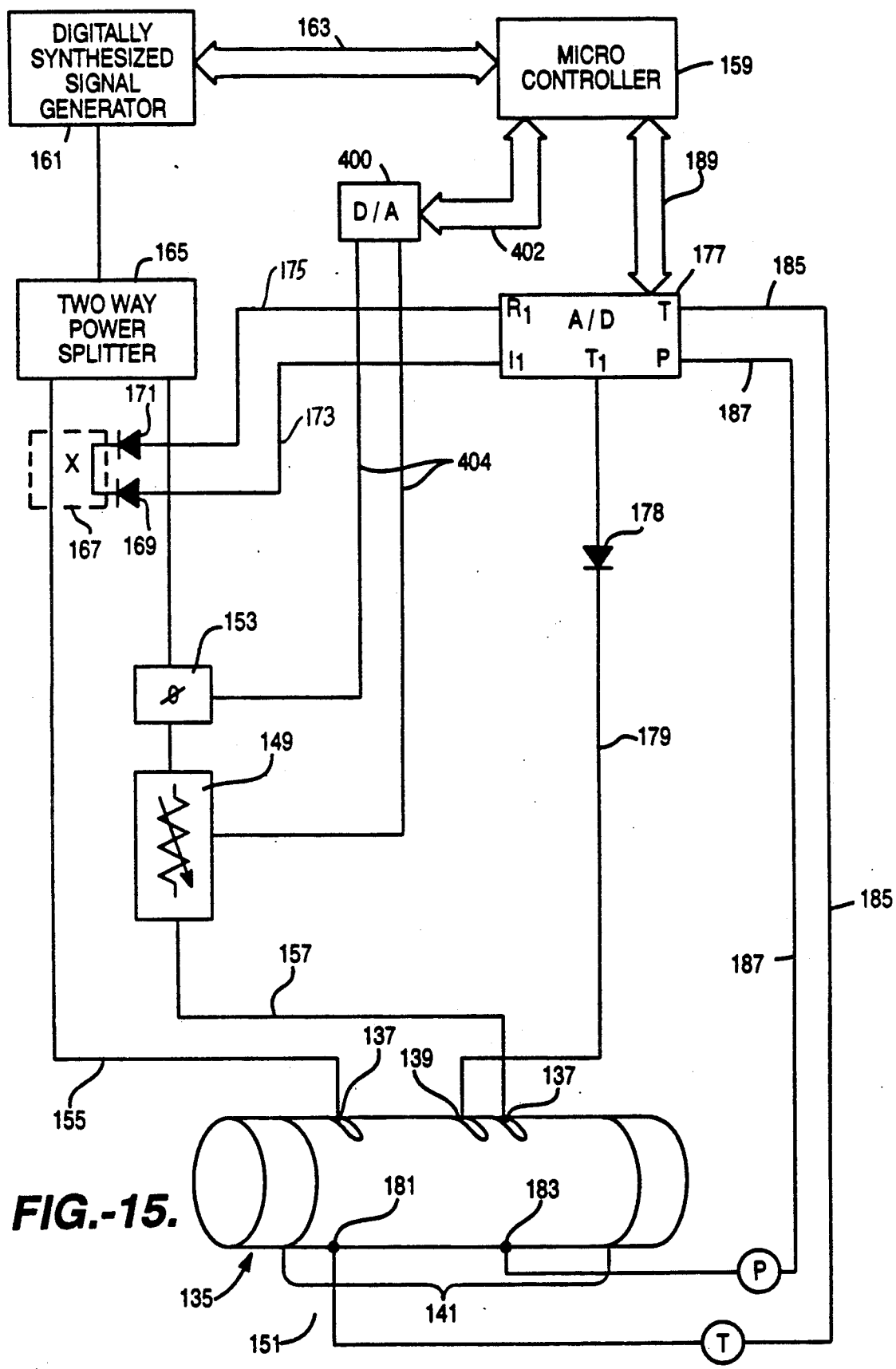
FIG. 15 is a block diagram of electronics usable with the monitor of FIGS. 12-13.

FIG. 15 shows a simple circuit which can be used with transducer 135. The input signal is split into two parts, one branch of which is passed through a phase shifter 153 and a variable attenuator 149. The optional phase shifter 153 is used to compensate for any phase differences between the two input signal lines 155 and 157. Electronics 151 includes a digital processor 159. The processor 159 is connected to a digitally synthesized source 161 by bus 163. The signal generator 161 is connected to transducer 135 by RF output lines 155 and 157 through a power splitter 165. The RF output line 155 is coupled through directional coupler 167 through detector diodes 169 and 171 to incident power input line 173 and reflected power input line 175, respectively, both of which are connected to provide inputs to an analog to digital (A/D) converter 177. Incident power input line 173 provides a signal representing the input RF power supplied on line 155 to transducer 135 to the A/D converter 177. Some of the input RF power supplied to transducer 135 is reflected by the transducer 135 back on line 155. Reflected power input line 175 provides a signal indicating the amount of this reflected power to the A/D converter 177. Transmitted power receiving aperture 139 spaced from the transmitting apertures 137 on the transducer 135 is connected by transmitted power input line 179 to the A/D converter 177 through detector 178. The receiving aperture 139 provides a signal to the A/D converter 177 on line 179 representing the portion of the RF power input transmitted through the transducer 135. Temperature and pressure sensing elements 181 and 183 on the transducer 135 similarly provide temperature and pressure input signals on line 185 and 187 to the A/D converter 177. Bus 189 connects the A/D converter 177 and the processor 159 for bidirectional communication. The processor 159 is connected to a digital to analog (D/A) converter 400 by the bus 402. D/A converter 400 provides a control signal on lines 404 for varying the attenuation of variable attenuator 149 and the phase shifter 153.

Instead of a digitally synthesized source, a sweep generator, a voltage controlled oscillator, or a current controlled oscillator could be used. The setup shown in FIG. 15 could be simplified in many practical applications. It is given in its general form here in order to demonstrate the kinds of measurements one would need to fully characterize the dielectric properties of the sample.

Figure 2:
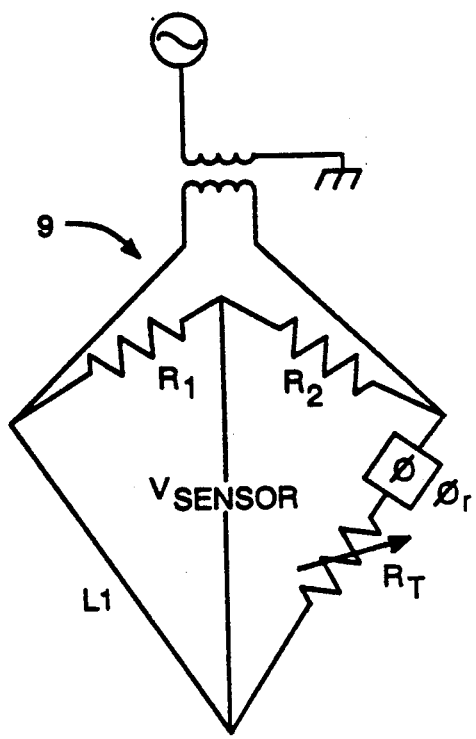
FIG. 2 is a schematic diagram of a circuit used to increase sensitivity of the FIG. 1 generalized composition monitor.
Figure 16:
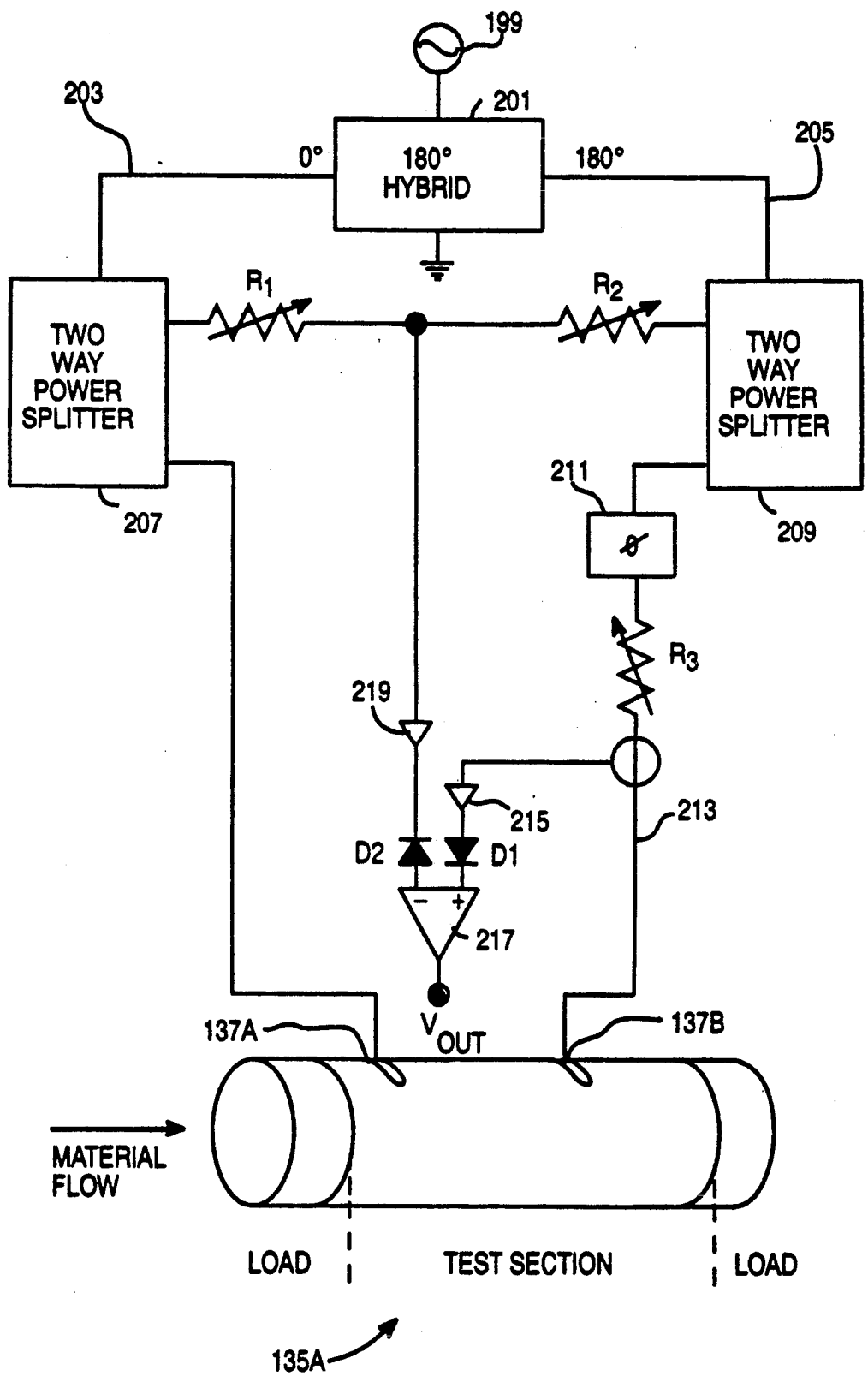
FIG. 16 is a second embodiment of the invention, comprising a block diagram of a second form of electronics usable with a modification of the monitor of FIGS. 12-13.

Embodiment 2—FIG. 16 illustrates an electronics block diagram with which this embodiment could be realized. This embodiment uses a transducer 135A, which is like the transducer shown in FIGS. 12 and 13, but with only a pair of apertures 137A and 137B. Aperture 137A is a transmitting aperture, and aperture 137B is a receiving aperture. Another difference between Embodiments 1 and 2 is that Embodiment 2 implements a resistive balancing network as illustrated in FIG. 2 to adjust the overall sensitivity of the system. By adjusting the resistance ratio between variable resistors $R_1$ and $R_2$ virtually any sensitivity can be achieved. A digitally synthesized source 199 has its output signal split using a 180° hybrid 201 connected by lines 203 and 205 to in-phase dividers 207 and 209. The dividers 207 and 209 provide their respective divided phase signals to resistors R1 and R2. Divider 207 supplies its other signal to the transmitting aperture 137A of the transducer 135A. The other signal from divider 209 is supplied through a phase shifter 211 and a variable resistor R3 to allow adjustment. The output signal from the receiving aperture 137B of the transducer 135A on line 213 is combined with the signal from divider 209 and supplied through operational amplifier 215 and diode D1 to the positive input of differential amplifier 217. Commoned outputs from the variable resistors R1 and R2 are supplied through operational amplifier 219 and diode D2 to the negative input of differential amplifier 217. The output from differential amplifier 217 provides an indication of the dielectric constant of the material flowing through the transducer 135A.

Instead of a digitally synthesized source, a sweep generator, a voltage controlled oscillator, or a current controlled oscillator could be used. The setup shown in FIG. 16 could be simplified in many practical applications. It is given in its general form here in order to demonstrate the kinds of measurements one would need to fully characterize the dielectric properties of the sample.

Figure 17:
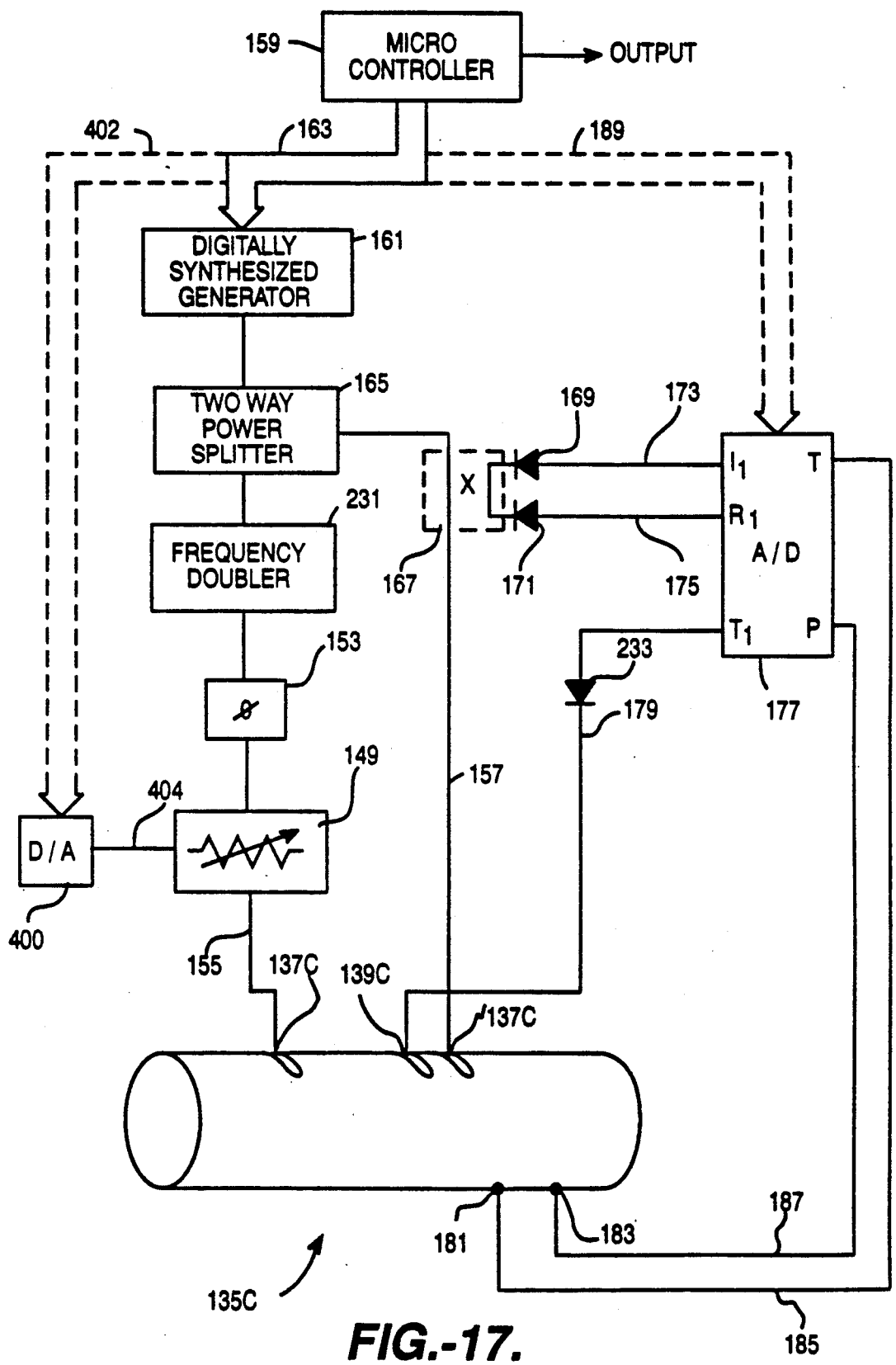
FIG. 17 is a third embodiment of the invention, comprising a block diagram of a third form of electronics usable with the monitor of FIGS. 12-13.

Embodiment 3—FIG. 17 illustrates an electronics block diagram for this embodiment. This embodiment uses a transducer 135C like the transducer shown in FIGS. 12 and 13, except that receiving aperture 139C is positioned equidistant between transmitting apertures 137C. The difference between Embodiment 1 and Embodiment 3 is that the latter is driven by two signals with different frequencies whereas the former is driven with a single frequency signal. The input signal is split into two parts, one branch of which is passed through a frequency doubler 231, a phase shifter 153 and a variable attenuator 149. The optional phase shifter 153 is used to compensate for any phase differences between the two input signal lines 155 and 157. A digital processor 159 is connected to a digitally synthesized source 161 by bus 163. The signal generator 161 is connected to transducer 135C by RF output lines 155 and 157 through a power splitter 165. The RF output line 157 is coupled through directional coupler 167 through detector diodes 169 and 171 to incident power input line 173 and reflected power input line 175, respectively, both of which are connected to provide inputs to an analog to digital (A/D) converter 177. Incident power input line 173 provides a signal representing the input RF power supplied on line 157 to transducer 135C to the A/D converter 177. Some of the input RF power supplied to transducer 135C is reflected by the transducer 135C back on line 157. Reflected power input line 175 provides a signal indicating the amount of this reflected power to the A/D converter 177. Transmitted power receiving aperture 139C spaced from the transmitting apertures 137C on the transducer 135C is connected by transmitted power input line 179 through diode 233 to the A/D converter 177. The receiving aperture 139C provides a signal to the A/D converter 177 on line 179 representing the portion of the RF power input transmitted through the transducer 135C. Temperature and pressure sensing elements 181 and 183 on the transducer 135 similarly provide temperature and pressure input signals on line 185 and 187 to the A/D converter 177. Bus 189 connects the A/D converter 177 and the processor 159 for bidirectional communication. The processor 159 is connected to a digital to analog (D/A) converter 400 by the bus 402. D/A converter 400 provides a control signal on line 404 for varying the attenuation of variable attenuator 149.

Instead of a digitally synthesized source, a sweep generator, a voltage controlled oscillator, or a current controlled oscillator could be used. The setup shown in FIG. 17 could be simplified in many practical applications. It is given in its general form here in order to demonstrate the kinds of measurements one would need to fully characterize the dielectric properties of the sample.

SIMPLIFIED BALANCED BRIDGE EMBODIMENTS

The embodiments described thus far have multiple signal paths and resistive terminations. They operate as balanced bridge networks where the multiple input signal paths are balanced by adjusting the frequency and the attenuation in one arm until a null is produced at a characteristic frequency related to the permittivity of the material. This method of operation can be simplified to produce a set of embodiments where the amplitude balancing between the two interfering electromagnetic waves is unnecessary. These embodiments use reactive loads and a single transmitting aperture in the manner illustrated by FIG. 5.

Transmitting apertures in the test section induce electromagnetic wave propagation in both directions in the waveguide. If the two oppositely directed waves are reflected back into the test section by reactive loads at the ends of the test section, they will interfere with one another. In fact, at specific frequencies, a standing wave interference pattern will be induced in the test section. The receiving aperture will sample the phase and magnitude of this standing wave pattern. At certain characteristic frequencies, the interference pattern is either constructive or destructive and recognizable peaks or nulls are measured in the insertion loss spectrum. The measured characteristic frequencies determine the permittivity of the material in the test section.

Several examples of embodiments which realize this simplified method are described below. Many other embodiments of the simplified balanced bridge method are possible.

Figure 18:
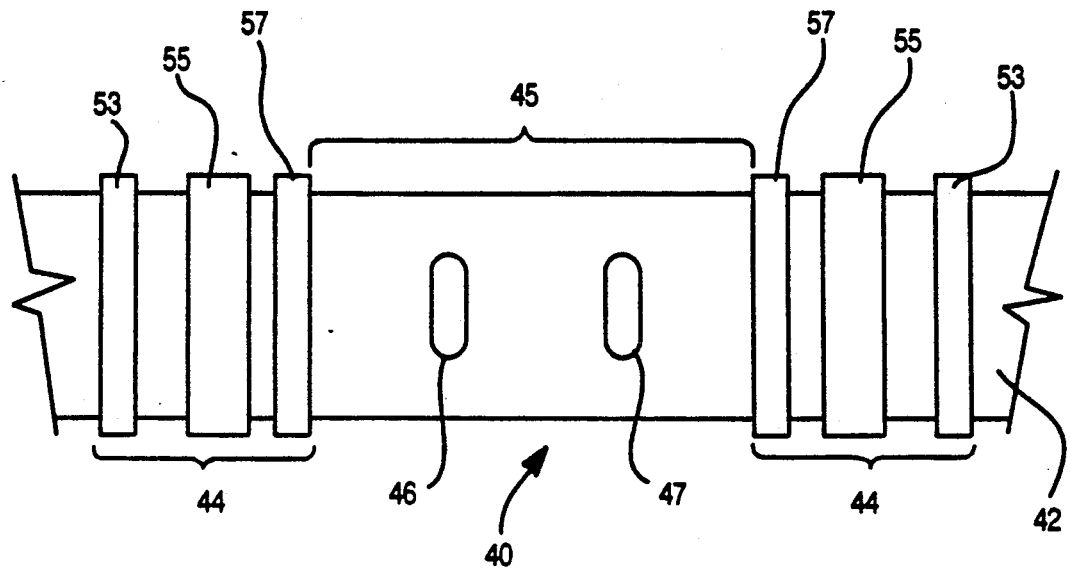
FIGS. 18 and 19 are side and cross-section views of a fourth embodiment of a monitor in accordance with the invention.
Figure 19:
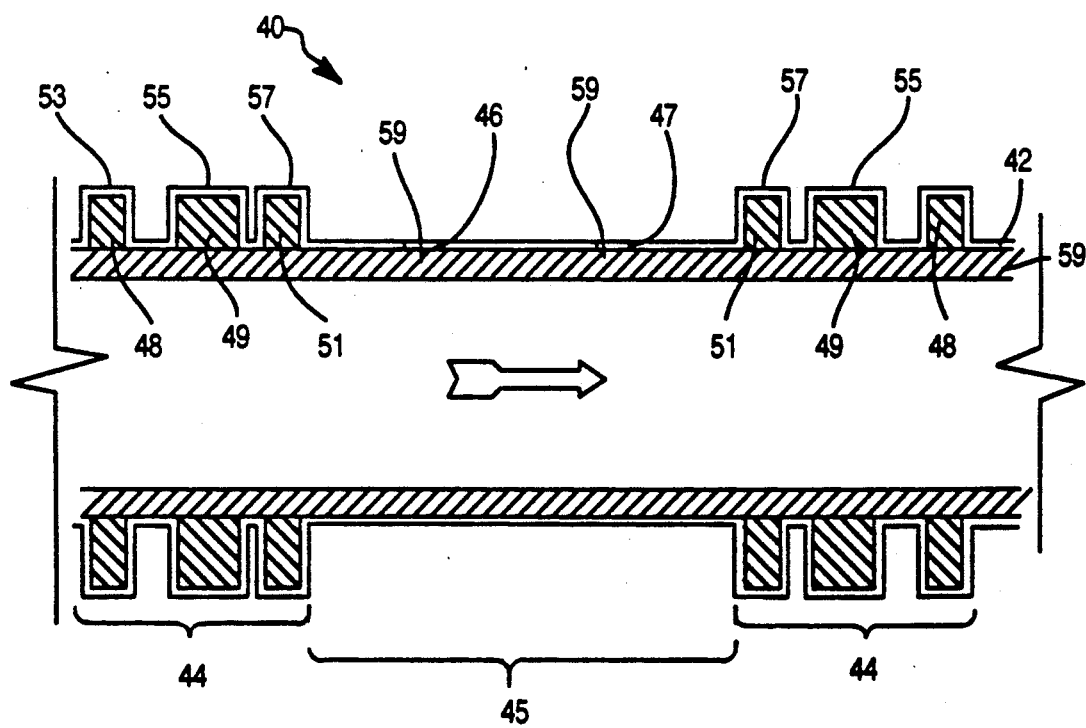

Embodiment 4—The cross section of one embodiment of the simplified balanced bridge method is illustrated in FIGS. 18 and 19. In this embodiment the electrical discontinuities take the form of two band reject filters 44 separated by a fixed distance. Transmission and receiving apertures 46 and 47 are placed between these filters 44 in test section 45. The filters 44 are designed to impede the propagation past them of electromagnetic energy within a certain frequency range. If the test section 45 is operated at frequencies within this band, then the energy is reflected back into the test section 45. The band reject filters 44 are constructed by making several cuts 47, 49, and 51 in the metal waveguide 42 of varying lengths separated by certain distances. These cuts 47-51 are enclosed by metal enclosures 53, 55, 57 to prevent radiative losses. A sleeve 59 of an insulating material, such as ceramic, is inserted inside the waveguide 42 to maintain a simple internal geometry in transducer 40 and to isolate the test material from electronic signal lines.

Obviously, this is just one example of the many ways a reactive termination can be realized.

Figure 20:
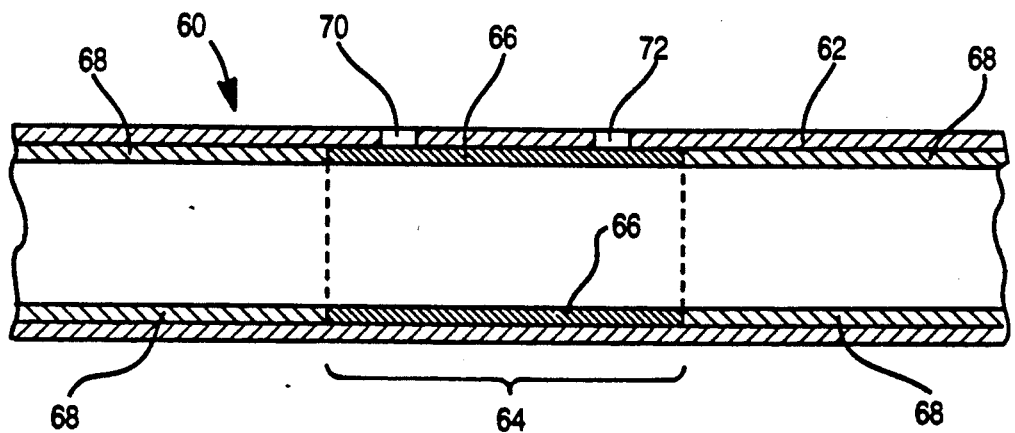
FIG. 20 is a cross-section view of a fifth embodiment of a monitor in accordance with the invention.

Embodiment 5—FIG. 20 shows another embodiment of the monitor utilizing the simplified balanced bridge measurement method. In the monitor transducer 60, waveguide 62 is lined on the inside with different dielectric materials 66 and 68. Test section 64 is lined with a material 66 having a very different dielectric constant than material 68 outside the measurement section 64. The result is to create electrical discontinuities. The discontinuities reflect much of the propagating electromagnetic signal back into the test section, effectively isolating the test section 64. Transmitting aperture 70 and receiving aperture 72 are provided in the metal waveguide over the first insulating material 66. In practice, the different dielectric materials 66 and 68 can be implemented with ceramics or plastics. Sleeve 68 could even be a metal.

Figure 21:
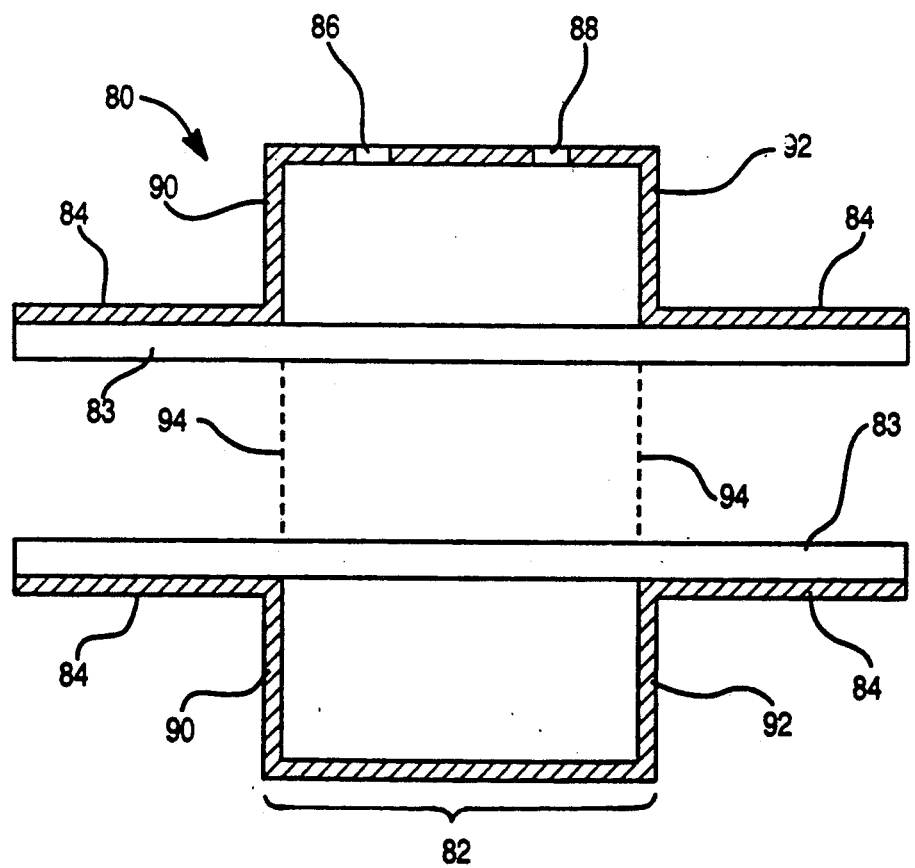
FIG. 21 is a cross-section view of a sixth embodiment of a monitor in accordance with the invention.

Embodiment 6—FIG. 21 shows another embodiment 80 using the simplified balanced bridge measurement method. In FIG. 21, monitor transducer 80 has a physically larger waveguide test section 82 connected to waveguide section 84. An electrically insulating sleeve 83 lines the waveguide 84 and passes through the center of the waveguide test section 82 with no change in diameter. Transmitting aperture 86 and receiving aperture 88 are located within the waveguide test section 82. The signal frequency above which waveguide test section 82 will propagate, called the cutoff frequency, is lower than that of waveguide section 84. If the operating frequency of transducer 80 is kept lower than the cutoff frequency of waveguide 84 but above that of test section 82, the junctions 90 and 92 where the waveguide changes size act as very efficient energy reflectors. Thus, junctions 90 and 92 act as the electrical discontinuities 94 which electrically isolate the test section 82 and at characteristic frequencies result in standing wave interference patterns being established in test section 82.

Figure 22:
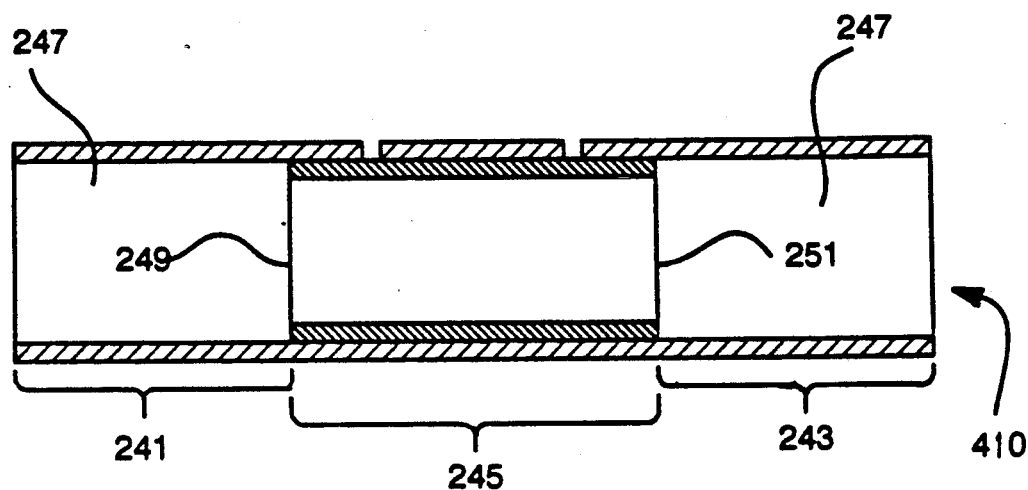
FIGS. 22 and 23 are cross-section and end views of a seventh embodiment of a monitor in accordance with the invention.
Figure 23:
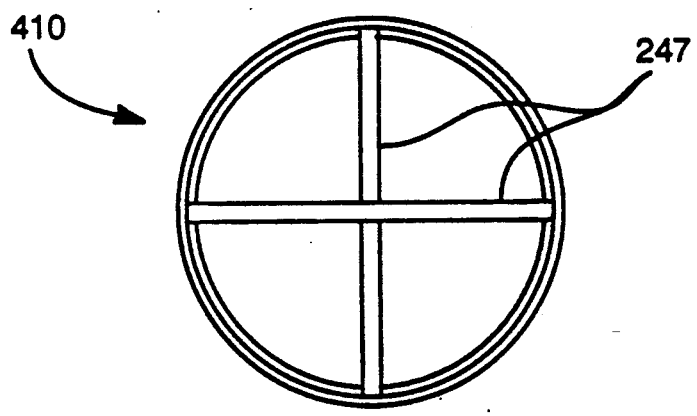
Figure 24A:
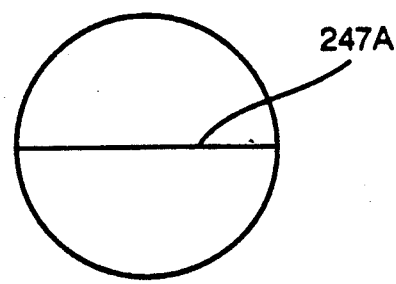
FIGS. 24a-24h are end views of modifications to the monitor of FIGS. 23-24.
Figure 24B:
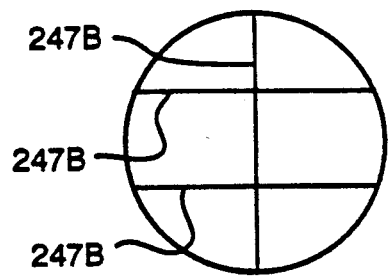
Figure 24C:
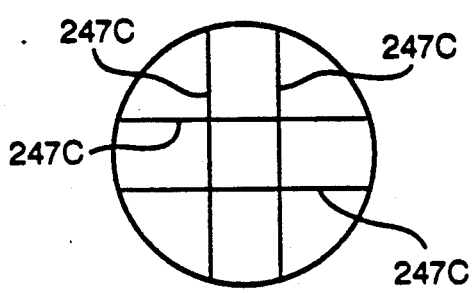
Figure 24D:
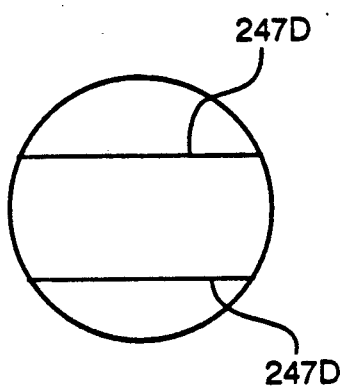
Figure 24E:
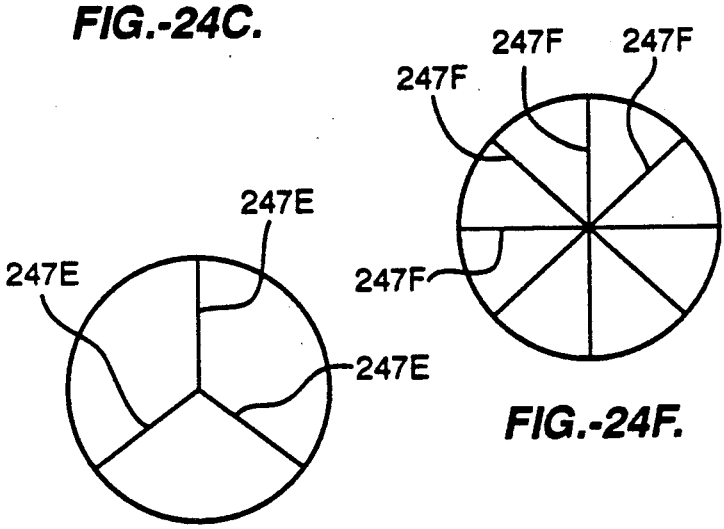
Figure 24F:
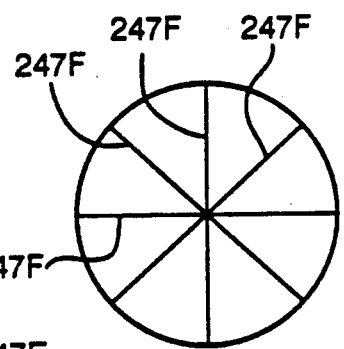
Figure 24G:
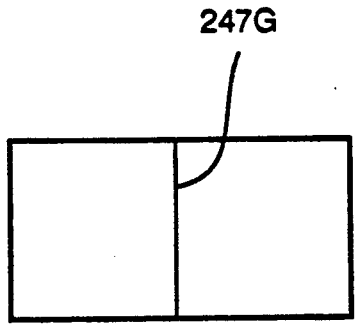
Figure 24H:
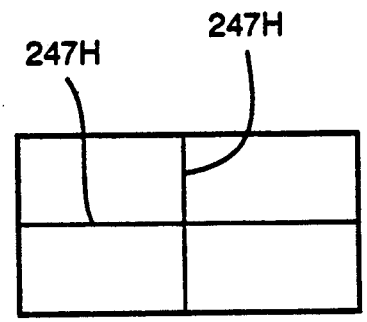

Embodiment 7—FIGS. 22 and 23 show another embodiment of a transducer 410 using the simplified balanced bridge method. This embodiment works similarly to Embodiment 6 in that the waveguide reactive load sections 241 and 243 beyond test section 245 have a higher cutoff frequency than does the test section 245. This is accomplished by segmenting the load segments 241 and 243 into smaller parts using metal plates 247. Thus, embodiment 7 is invasive whereas the others are not. The test section 245 of this embodiment is constructed and operates in the same manner as the test section 64 in embodiment 5 (FIG. 20).

In operation, if the test section 245 is operated at a frequency below the cutoff frequency of the load sections 241 and 243 but above that of the test section 245, the propagating energy is reflected at junctions 249 and 251. Thus, junctions 249 and 251 act as the electrical discontinuities which electrically isolate the test section and at characteristic frequencies result in standing wave interference patterns being established in the test section 245.

In FIGS. 22 and 23, two metal plates 247 are used to segment the load section into four parts. As shown in FIGS. 24a-24h, many different orientations of metal plates 247a-247h are possible, all of which accomplish the same objectives: to electrically isolate the test section and to make it possible to implement the simplified balanced bridge approach.

Figure 25:
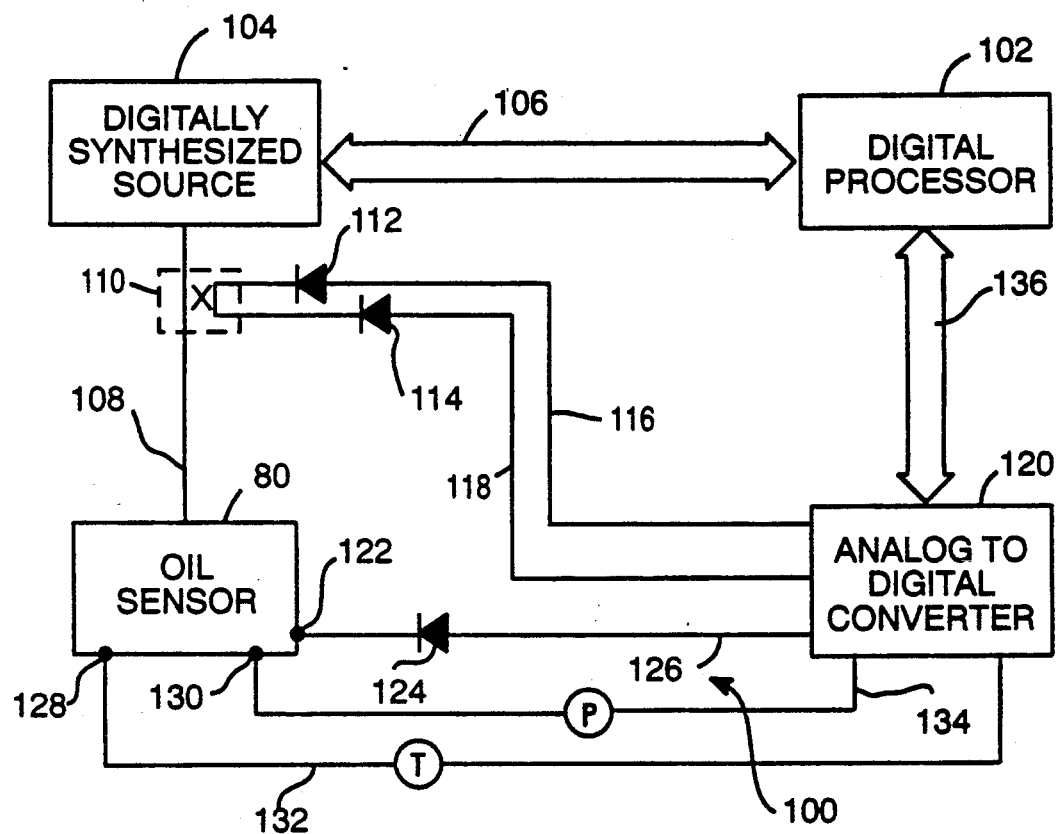
FIG. 25 is a block diagram of electronics which may be used with the monitors shown in FIGS. 18-24h.

FIG. 25 shows a simple electronics package which could be used with Embodiments 4, 5, 6, and 7. Electronics 100 includes a digital processor 102, implemented with any of a variety commercially available microprocessor integrated circuits. The processor 102 is connected to a digitally synthesized source 104 by bus 106. Instead of a digitally synthesized source, a sweep generator, a voltage controlled oscillator, or a current controlled oscillator could be used. The signal generator 104 is connected to transducer 80 by RF output line 108, it being understood that the transducer 40, 60 or 410 can be substituted for the transducer 80 shown. The RF output line 108 is coupled at 110 through detector diodes 112 and 114 to incident power input line 116 and reflected power input line 118, respectively, both of which are connected to provide inputs to an analog to digital (A/D) converter 120. Incident power input line 116 provides a signal representing the input RF power supplied on line 108 to the transducer 80 to the A/D converter 120. Some of the input RF power supplied to the transducer 80 is reflected by the transducer 80 back on line 108. Reflected power input line 118 provides a signal indicating the amount of this reflected power to the A/D converter 120. Transmitted power sensing element 122 spaced from the RF input line 108 on the transducer 80 is connected through diode 124 and transmitted power input line 126 to the A/D converter 120. The sensing element 122 provides a signal to the A/D converter 120 on line 126 representing the portion of the RF power input transmitted through the transducer 80. Temperature and pressure sensing elements 128 and 130 on the transducer 80 similarly provide temperature and pressure input signals on lines 132 and 134 to the A/D converter 120. Bus 136 connects the A/D converter 120 and processor 102 for bidirectional communication.

Figure 26:
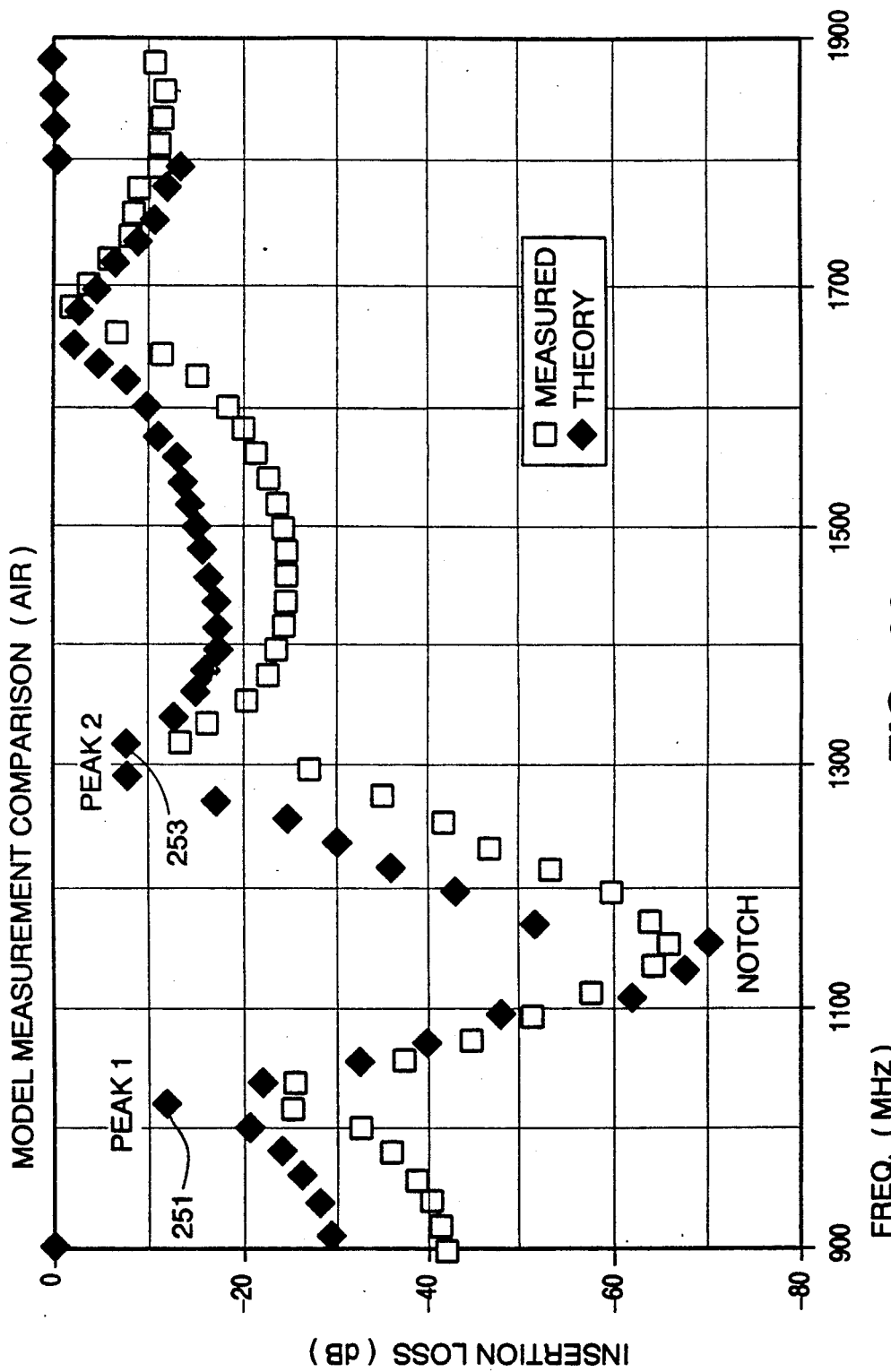
FIGS. 26-34 are graphs of experimental results obtained with a in accordance with the invention.
Figure 27:
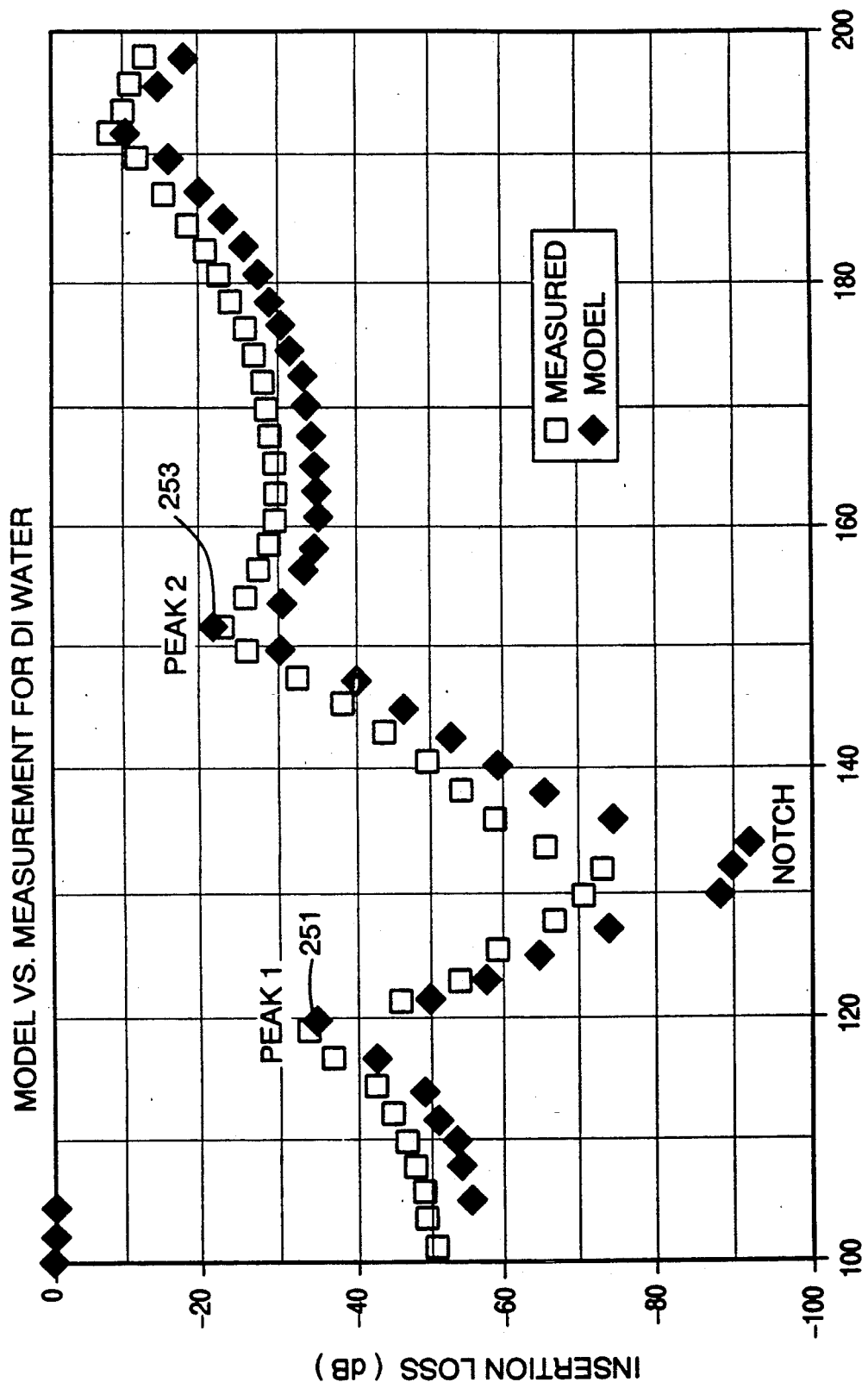

FIGS. 26 and 27 show typical measured insertion loss spectra achieved with the simplified balanced bridge technique using one input slot and electrical discontinuities to create an interference pattern in the test section. FIG. 26 shows a comparison of experimental measurements made of a prototype monitor similar to the transducer configuration of Embodiment 6 filled with air and the predicted spectrum of a simple model. FIG. 27 shows corresponding data when the prototype was filled with deionized water. Though the overall insertion loss values are not well predicted by the model, the peak positions 251 and 253 in each graph are predicted within 1%.

Figure 28:
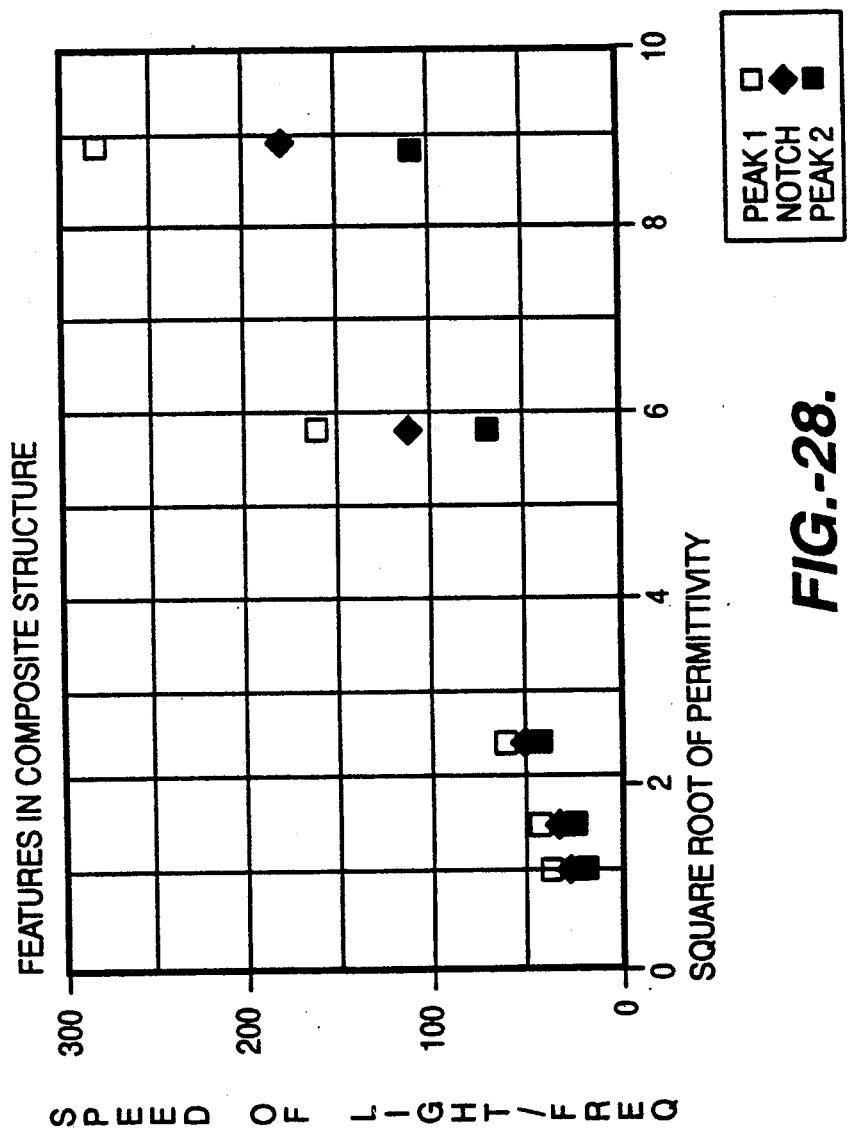

FIG. 28 shows a plot of the speed of light divided by frequency versus the square root of the permittivity of the material in the test region for a prototype of Embodiment 6. The relationship is nonlinear because the test section is dielectrically loaded with air and the insulating sleeve in addition to the test material. Thus, the effective permittivity of the test section is less than that of the material.

Figure 29:
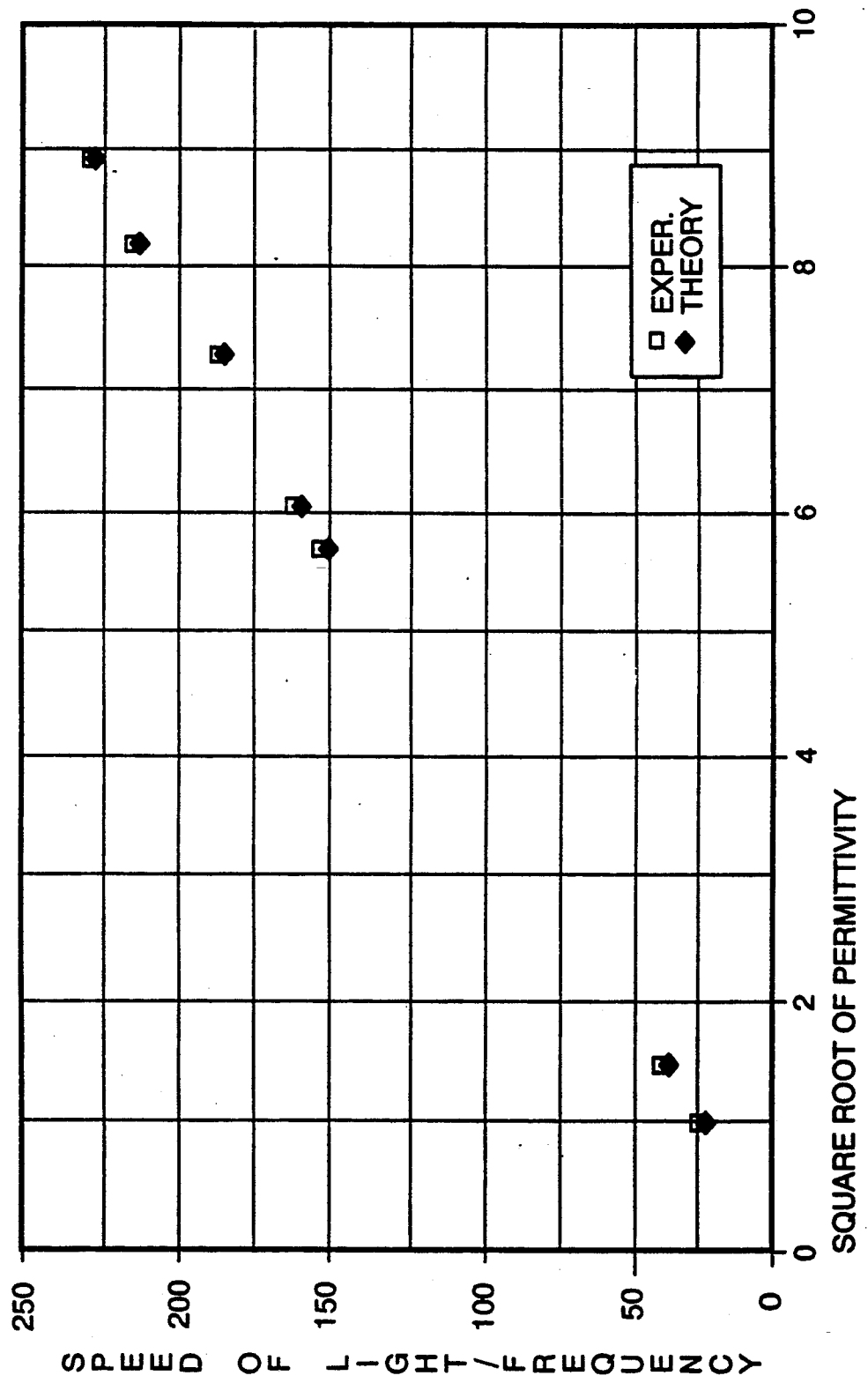

For embodiments of the concept such as Embodiments 4, 5, and 7 where the test material fills virtually all of the test section, the relationship between the resonant frequencies and the square root of the material permittivity is virtually linear. FIG. 29 shows the relationship for such a prototype compared to the predictions of a simple waveguide model. The model results are very close despite the fact that the predictions for the overall insertion loss values are poor. FIGS. 28 and 29 illustrate the simplicity with which the transduction of the measured characteristic frequencies to material permittivity is achieved with this invention.

Figure 30:
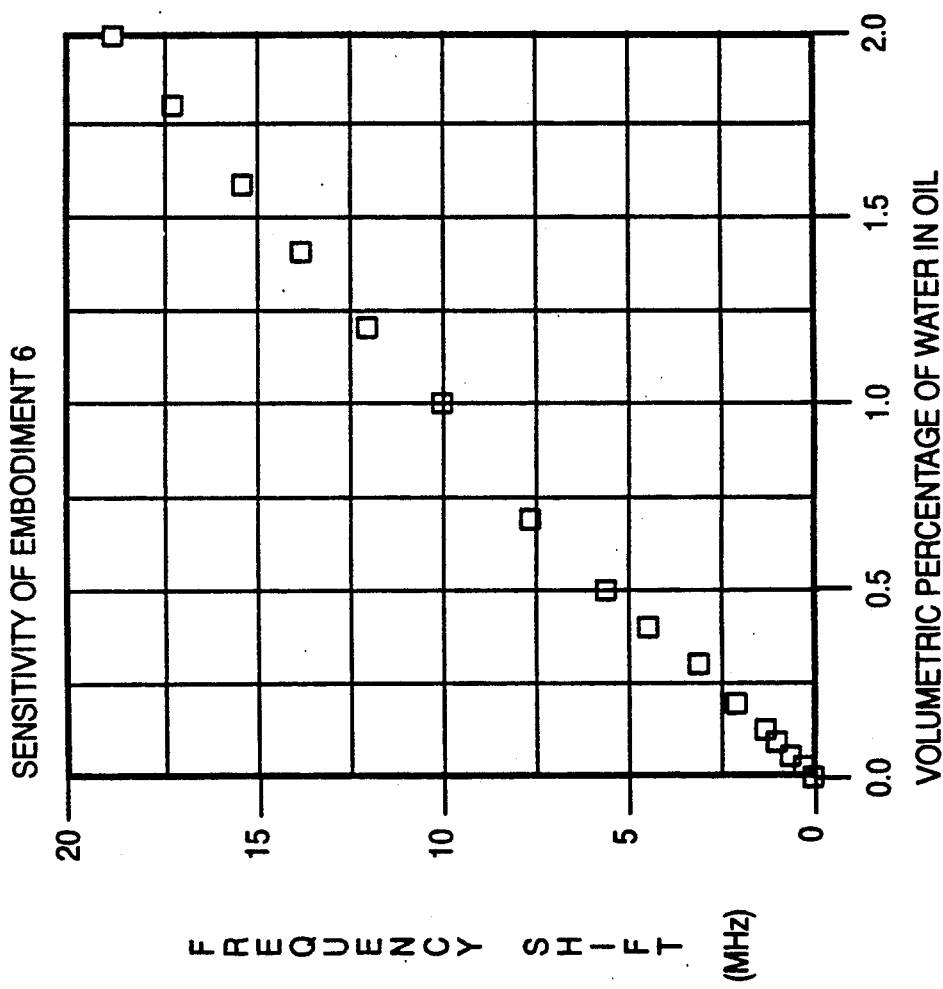
Figure 31:
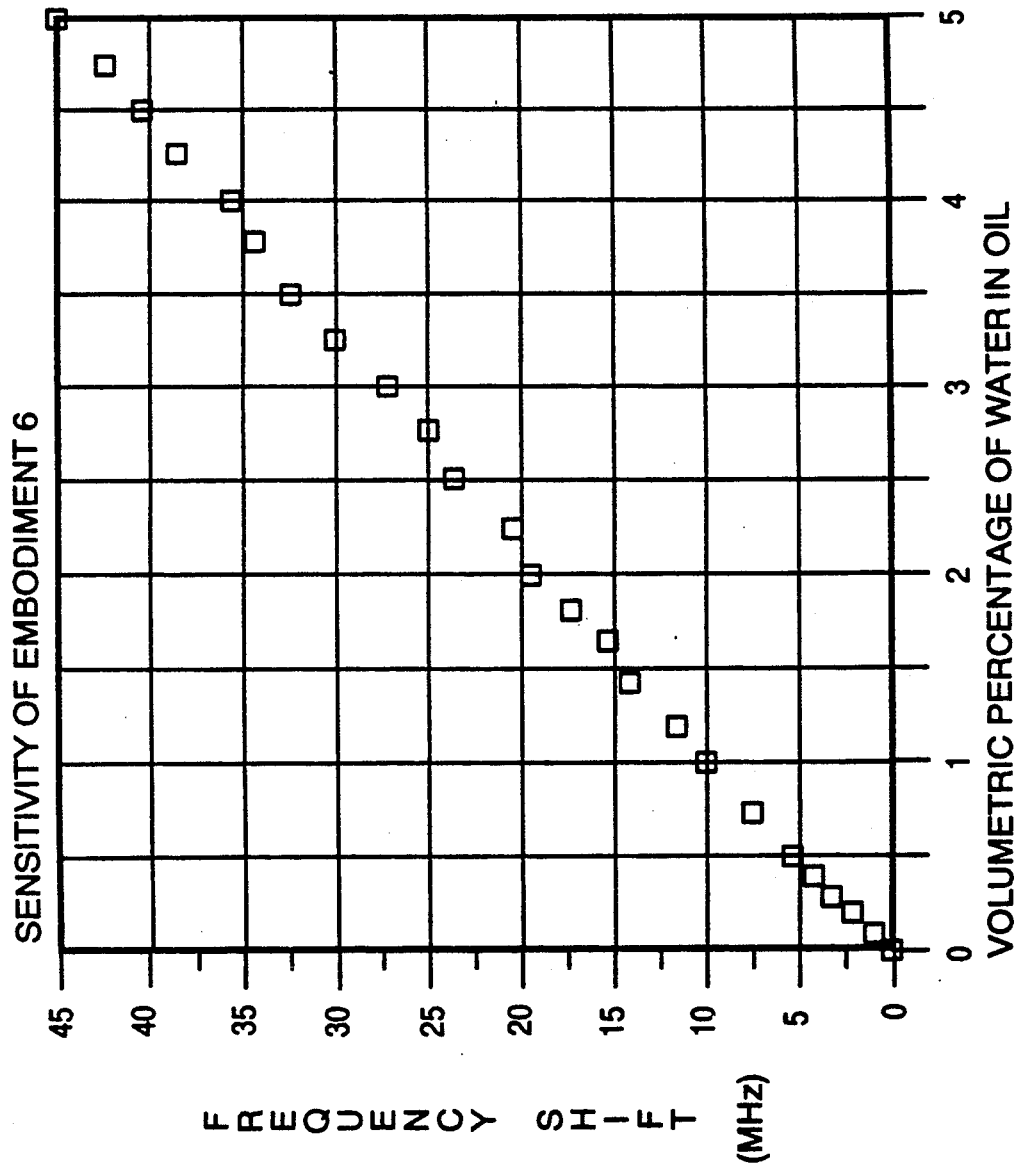
Figure 32:
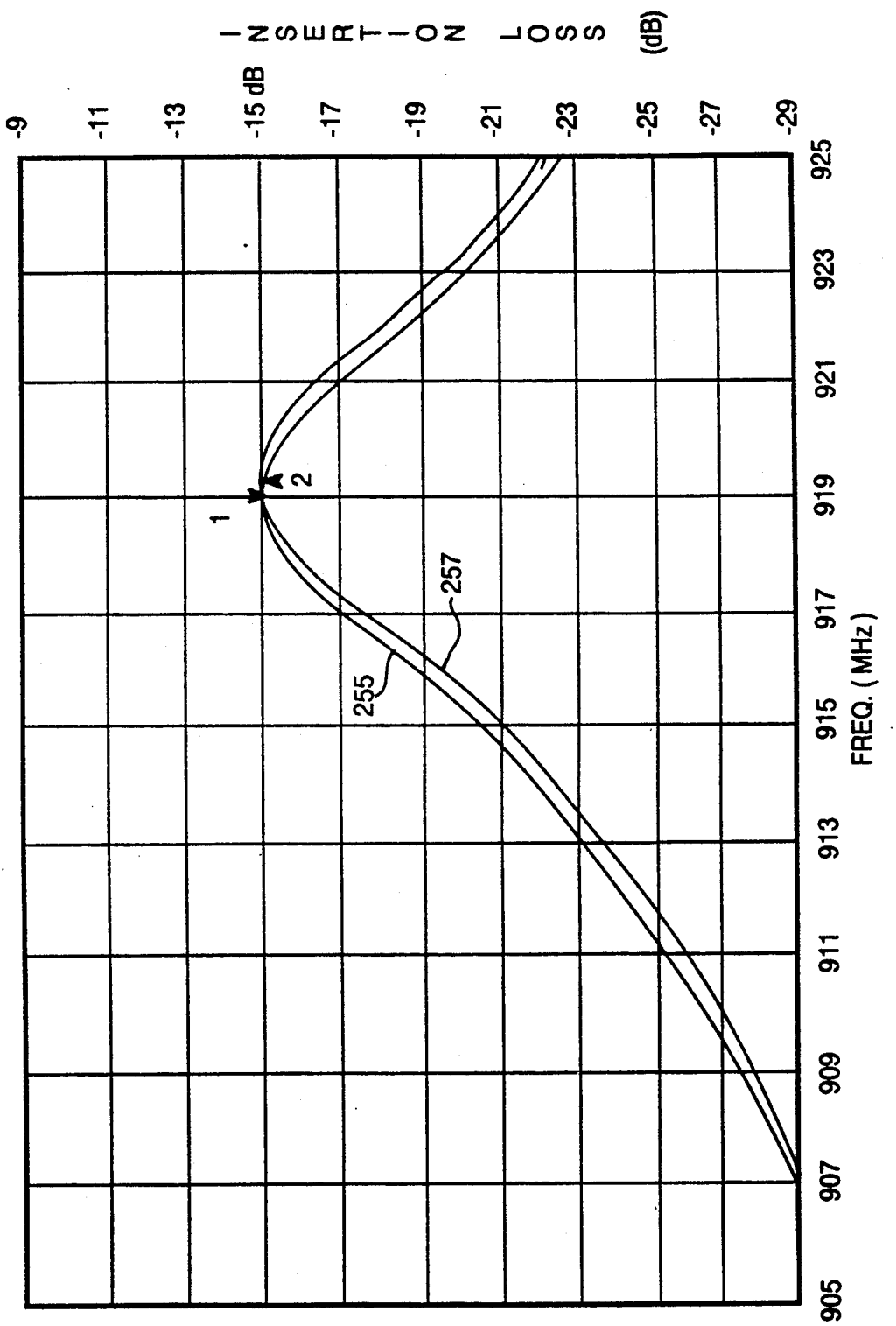

FIGS. 30 and 31 illustrate the accuracy with which the apparatus of this invention can be used to determine composition. These figures show the measured characteristic frequency shift of a prototype of Embodiment 6 when oil with very small percentages of water is added to it. These measurements indicate that the potential accuracy of such an apparatus to be better than 0.1% water in oil. With this level of accuracy the apparatus would be capable of accurate water determinations in crude oil for custody transfer applications in the petroleum industry. FIG. 32 shows the measured spectrum 255 for 0.025% water in oil compared to a curve 257 for pure oil. The higher frequency curve 257 is that for pure oil. Though the total frequency shift is only 0.4 MHz, it is resolvable. The shift in permittivity is about 0.077% and the corresponding shift in frequency is 0.044%.

Figure 33:
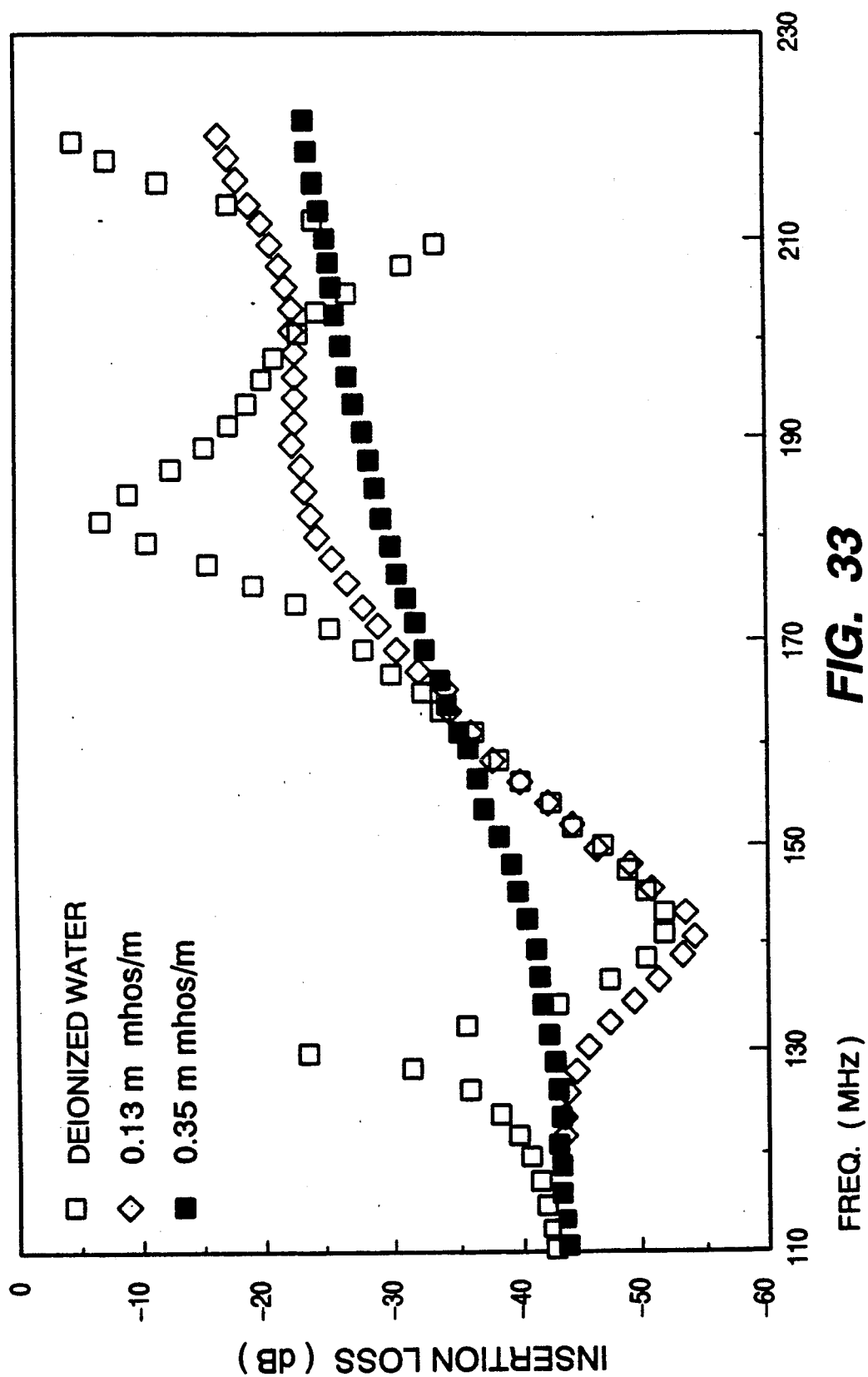
Figure 34:
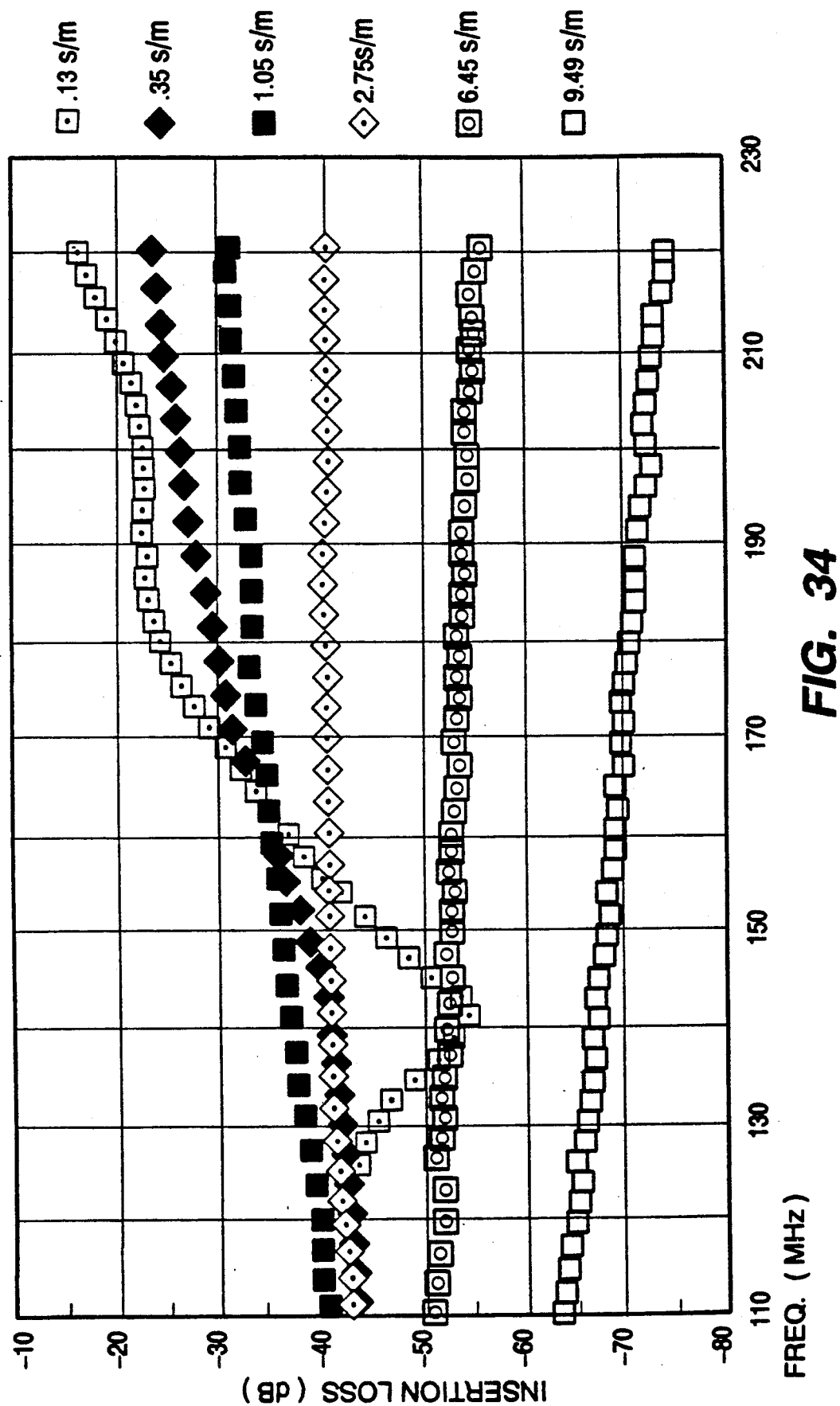

The electromagnetic interference concept around which the permittivity measurement method of this invention depends works best if the test material conductivity is not too high. If the material has a large dissipation factor, the propagating electromagnetic energy attenuates so quickly in the test section that a recognizable interference pattern cannot form. Hence, the characteristic frequencies cannot be measured by this technique nor can the fluid permittivity. FIG. 33 shows the measured insertion loss spectra of a prototype embodiment of this invention as a function of the conductivity of water. The measurements are made with a prototype monitor similar to the transducer configuration of Embodiment 6. For this prototype the characteristic peaks and nulls are hidden when the conductivity of the measured material approaches 0.35 mhos/m. When the material conductivity rises above this level, another technique must be used. FIG. 34 shows several spectra measured in the same prototype of higher conductivity water solutions. As these results show, at higher frequencies, the insertion losses are very sensitive to the conductivity level. At 220 MHz, the insertion loss increases by about 50 db when the conductivity is increased by 30 times. The dynamic range is even greater at higher operating frequencies. These results show that the apparatus illustrated by Embodiments 1-6 can be used to measure material conductivity when the conductivity is so high that permittivity measurements are not possible. The conductivity information can be related to material composition just as can permittivity. Given this added ability, the various possible embodiments of this invention can be used to measure any material or mixtures of materials where the dielectric properties vary over a wide range. The apparatus can handle virtually any conductivity level or permittivity that could be encountered in an industrial process material.

Embodiment 8—One of the problems with composition monitors applied to measurement of continuously flowing materials or mixtures is that the material composition is heterogeneous and unevenly mixed. This is especially true for applications involving mixtures of immiscible components having differing densities. Examples include solid/liquid mixtures such as slurries, liquid/gas mixtures such as steam or oil/water/gas, or even pure liquid mixtures such as oil/water. The difficulty is that most such monitors measure some aggregate physical property of the mixture such as the dielectric properties, the density, or optical properties and use this information to determine the composition. Unless there is a constant physical configuration of the components in the mixture at all times, such an approach will not work because the measured physical properties cannot be accurately related to composition. Uniform and thorough mixing of some sort is required for accurate composition monitoring of difficult mixtures containing immiscible fluids or components having differing densities. This invention is not immune to this problem because it too measures a physical property of the total mixture and relates it to the composition of that mixture.

Figure 35:
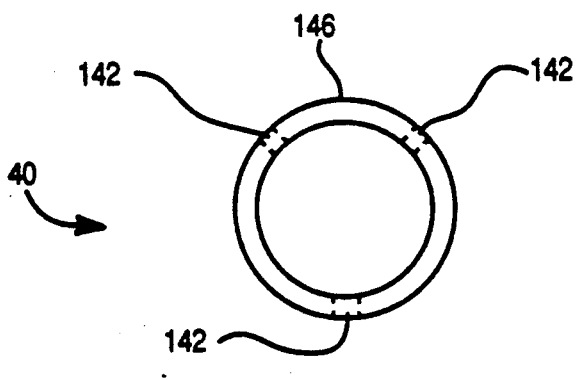
FIGS. 35-36 are end and side views of an eighth embodiment of a in accordance with the invention.
Figure 36:
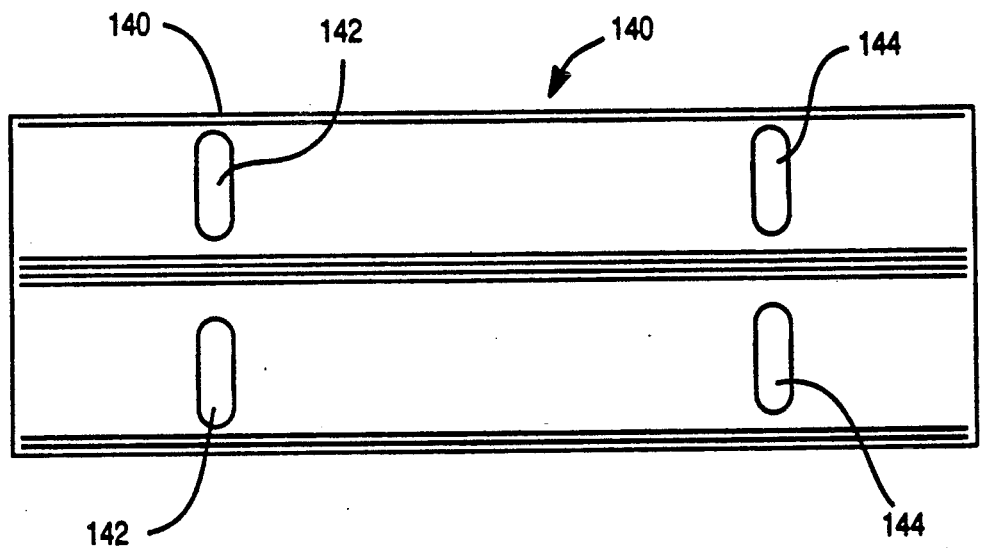

One aspect of this invention, however, is that it can be readily designed to determine when the measured mixture is uniformly mixed. This capability is achieved with the transducer embodiment 140 in FIGS. 35 and 36, in which transmitter aperture 142 and receiver aperture 144 pairs are evenly distributed around the circumference of the test section 146. It is a feature of this invention that by comparing the signals received by the receiver apertures 144, it determines if mixing is homogeneous. If the signals are the same, the material is uniformly mixed. If not, the material is inhomogeneous and the accuracy of the compositional determination will diminish accordingly. This arrangement would fail only when an axially symmetric mixture, such as annular flow, is present. This is not likely under most conditions. A composition monitor incorporating the transducer 140 can disable itself or initiate corrective action when uniform mixing is not present. Another alternative is to average the compositional determination made using the information from each of the aperture pair readings individually. In either case, errors will be reduced and more accurate totalized measurements will be possible. The multiple measurement aperture pair concept illustrated in transducer test section 140 can be implemented into Embodiments 1–7 in the same manner to give these embodiments the added capability of measuring material uniformity.

Figure 37:
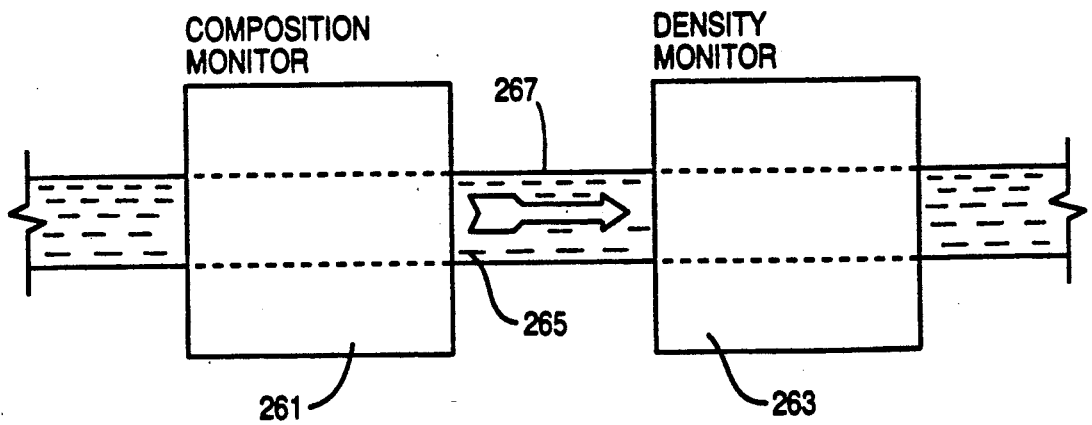
FIG. 37 is a schematic side view of a composition measuring system comprising a ninth embodiment in accordance with the invention.

Embodiment 9—The method and apparatus described thus far can measure a test material's temperature and pressure and its permittivity and/or conductivity. For many composition monitoring applications, this combination of measurements will be enough to determine material composition. For others, however, this information is not enough to completely determine composition. The composition of material mixtures consisting of four or more components having differing dielectric properties could not be determined by the Embodiments 1-8, though these embodiments could still be used as very accurate trend monitors. In special cases, the composition of even three component mixtures could not be measured exactly with these embodiments. One important example is oil, water, and gas mixtures. In order to extend the range of useful materials and applications to which the novel methods and apparatus described in this invention could be applied, an additional measurement means for determining material density is to be added to the RF dielectric measurement apparatus described as Embodiments 1-8. This new embodiment, Embodiment 9, is shown in FIG. 37. The RF dielectric composition monitor 261 and the density monitor 263 are connected in series with a pipe 265, through which the test material 267 can pass freely between the two measurement apparatuses.

RF dielectric composition monitor 261 could be any of the Embodiments 1-8 or any of the other possible embodiments consistent with the methods of dielectric measurement of this invention. Density monitor 263 could be any of the commercially available apparatus for measuring the density of materials flowing in a pipe. Two examples are Coriolis Force densitometers and the gamma ray densitometers. These systems require even mixing for accurate readings just as the waveguide dielectric transducer does. Thus, the construction of the transducer 140 is equally important for preventing errors in the density measurement of these devices.

An example of the relationship between mixture permittivity, mixture density, and mixture composition is described in the following formulas. The example illustrated is that of oil, water and gas mixtures.

x = volumetric ratio of component 1 (oil).
y = volumetric ratio of component 2 (water).
z = volumetric component ratio of component 3 (gas).

$$\text{Total volume ratio} = 1 = x + y + z \tag{2}$$

$$\text{Measured Density of Mixture} = ax + by + cz \tag{3}$$

where
a = density of component 1
b = density of component 2
c = density of component 3 (0 for gas)

Equation (2) simplifies to $$\text{Measured Density} = ax + by \tag{4}$$

The Bruggeman model relates the dielectric constant of a two-component mixture to the dielectric constant of the components as follows:

$$\frac{\epsilon_2 - \epsilon_{p1}}{\epsilon_m - \epsilon_{p1}} \left(\frac{\epsilon_m}{\epsilon_2}\right)^{\frac{1}{3}} = 1 - \Phi_1 \rightarrow \epsilon_2 = F(\epsilon_m, \epsilon_{p1}, \phi_1)$$

where
$\epsilon_2$ = electric constant of two component mixture
$\epsilon_m$ = dielectric constant of the continuous medium of emulsion (assume it is component 1)
$\epsilon_{p1}$ = dielectric constant of first dispersed phase (assume it is component 2)
$\phi_1$ = volumetric ratio of first dispersed phase in continuous medium (this equals y/(x+y) under above assumptions)

This scheme can be generalized to three components with an iterative solution as follows $$\epsilon_3 = F(F(\epsilon_m, \epsilon_{p1}, \phi_1), \epsilon_{p2}, \phi_2)$$

where
$\epsilon_3$ = measure dielectric constant of the total mixture
$\epsilon_{p2}$ = dielectric constant of second dispersed phase (assume it is component 3)
$\phi_2$ = volumetric ratio of second disperse phase (equals z in this case)

We have the following relationship for the dielectric constant:

$$\epsilon_{meas.} = F(F(\epsilon_{comp1}, \epsilon_{comp2}, y/x+y), \epsilon_{comp3}, z) \quad \text{Equation (5)}$$

From a measurement of dielectric constant and density, equations (2), (4) and (5) can be used to determine what the individual component ratios are. The Bruggeman-Hanai relationship has been represented here to illustrate the relationship between dielectric constant and component volumetric ratios. Other relationships could be used, as could calibration curves.

Figure 38:
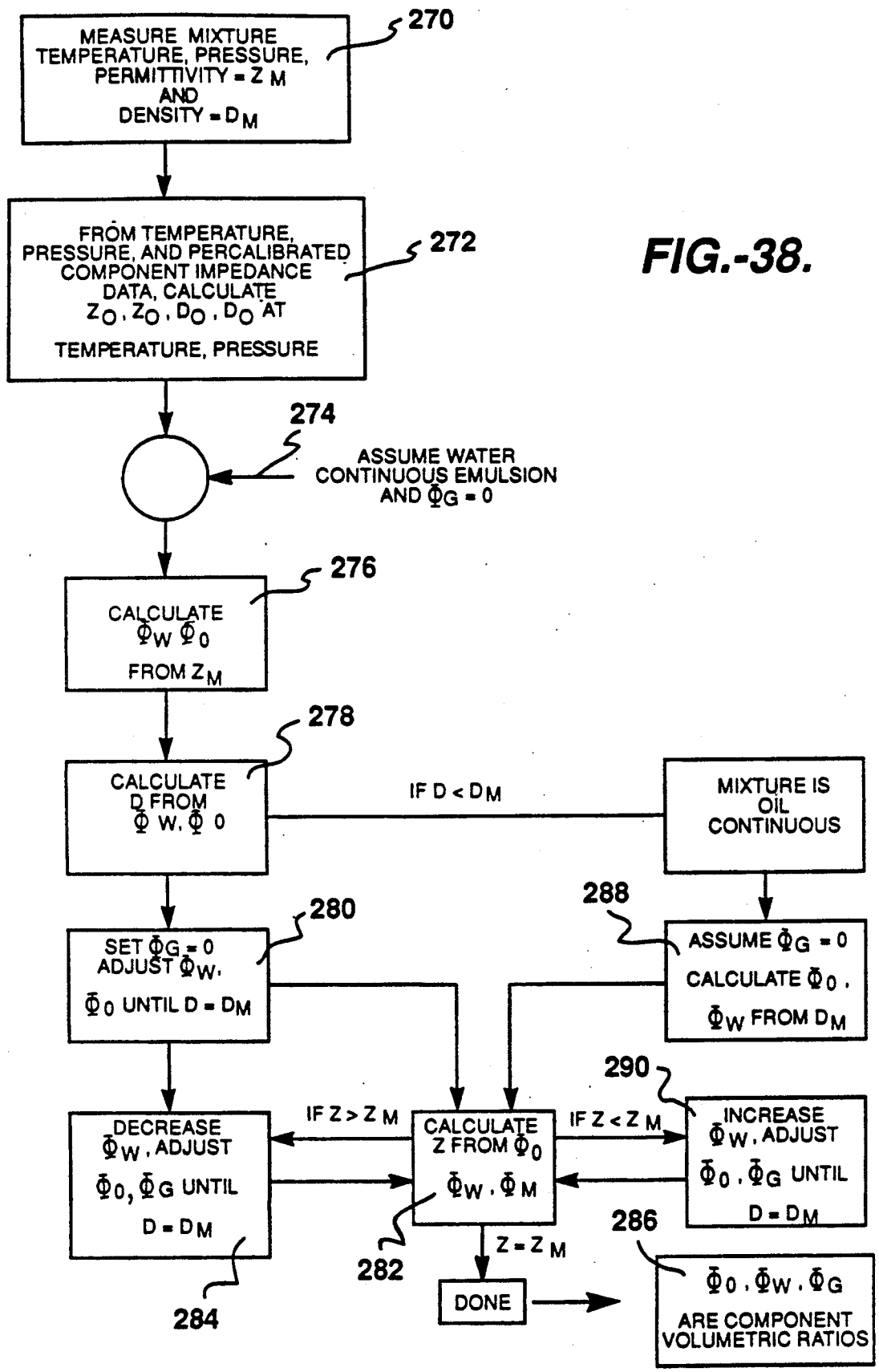
FIG. 38 is a flow diagram of a transduction process as carried out with the system of FIG. 37.

FIG. 38 shows a particular process analysis algorithm in the use of Embodiment 8 as shown in FIG. 37. The algorithm is applicable for oil, water and gas applications where the free gas content remains below about 20% by volume. Another algorithm must be used if the gas ratio is higher than 20%. The measured mixture properties are permittivity and/or conductivity, density, temperature, and pressure. The variables used in FIG. 38 are the volumetric ratio of gas, $\phi_G$, the volumetric ratio of water, $\phi_W$, the volumetric ratio of oil, $\phi_O$, measured mixture permittivity (or measured mixture conductivity), $Z_M$, and measured mixture density, $D_M$. The temperature, pressure, permittivity and density of the mixture are measured at 270. $Z_O$, $Z_W$, $D_O$, and $D_W$ are calculated from the measured temperature, pressure and precalibrated component impedance data at 272. From these results, and assuming that the mixture is a water continuous emulsion and that no gas is present in the mixture ($\phi_G = 0$), as indicated at 274, $\phi_W$ and $\phi_O$ are calculated from $Z_M$ at 276. From these results, a trial density D is calculated at 278. If the density D is $>D_M$, $\phi_G$ is increased and $\phi_W$ and $\phi_O$ are adjusted until $D = D_M$ at 280. From these values of $\phi_O$, $\phi_W$, and $\phi_G$, a trial value of Z is calculated at 282. If the trial $Z < Z_M$, $\phi_W$ is decreased and $\phi_O$ and $\phi_G$ are adjusted until $D = D_M$ at 284. The trial Z is then calculated again at 282. Steps 282 and 284 are repeated until $Z = Z_M$, which completes the process, resulting in the correct values of $\phi_O$, $\phi_W$ and $\phi_G$ at 286. Returning to step 278, if the trial $D < D_M$, the mixture is oil continuous, i.e., the assumption at 274 is incorrect. In that case, $\phi_G$ is assumed $=0$, and $\phi_O$ and $\phi_G$ are calculated from $D_M$ at 288. Step 282 is then carried out, and if the calculated trial $Z < Z_M$, $\phi_W$ is increased and $\phi_O$ and $\phi_G$ are adjusted until $D = D_M$ at 290. Steps 282 and 290 are repeated until the trial $Z = Z_M$, giving the correct values of $\phi_O$, $\phi_W$ and $\phi_G$ at 286.

Figure 39:
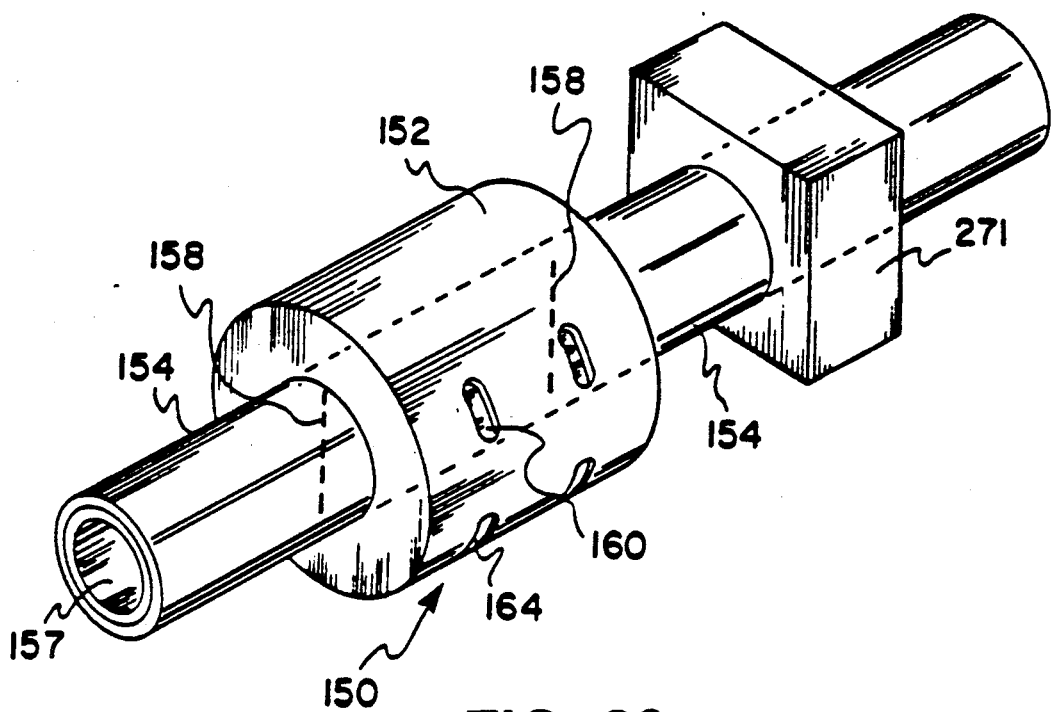
FIGS. 39-40 are side and end views of a monitor system in accordance with the invention.
Figure 40:
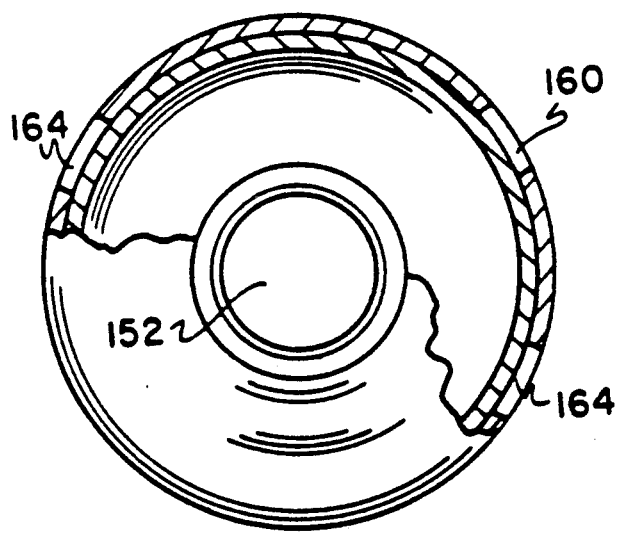

FIGS. 39 and 40 show a monitor transducer 150 which combines the features discussed previously for Embodiments 6, 8, and 9. The transducer 150 has a test section 152 of enlarged diameter, similar to the section 82 in the FIG. 21 embodiment. Waveguide sections 154 on either side of the test section 152 have a smaller diameter, for example, half that of the test section 152. A constant diameter insulating sleeve 157 extends through the pipe sections 154 and the enlarged diameter test section 152. The diameter change between the test section 152 and the sections 154 creates a pair of discontinuities 158. Energy from RF input apertures 160, 162, and 164 that is coupled into test section 152 is substantially confined within the transducer 150 by the discontinuities 158. Density monitor 271 is connected to the transducer 150 by the waveguide pipe section 154. In addition, if a means for measuring mixture flow rate is connected to the composition measurement system, the combined system would be capable of determining the total production volume of each individual component over a period of time.

Figure 41:
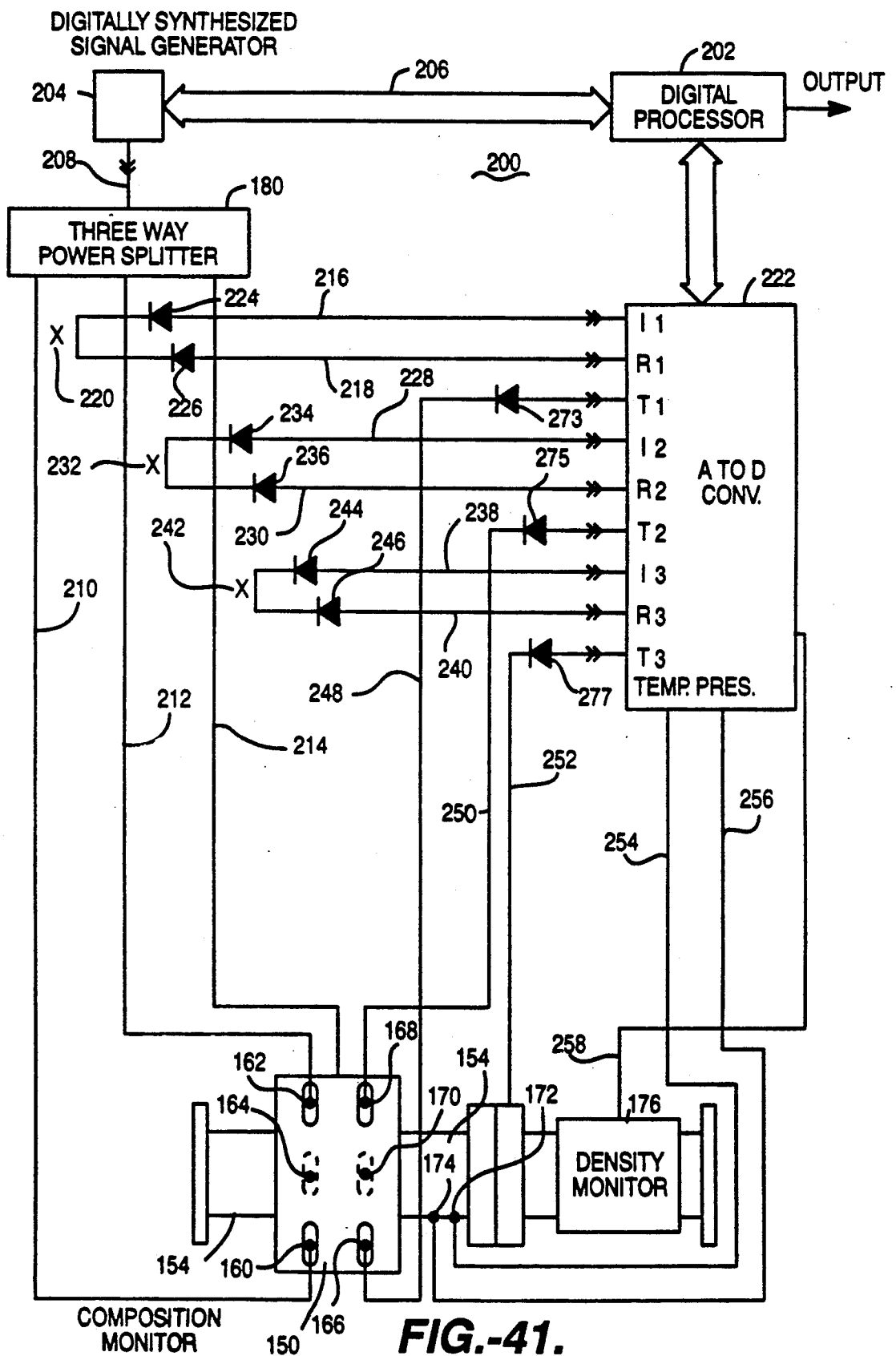
FIGS. 41-43 are block diagrams of electronics for use with the monitor system illustrated in FIGS. 39-40.
Figure 42:
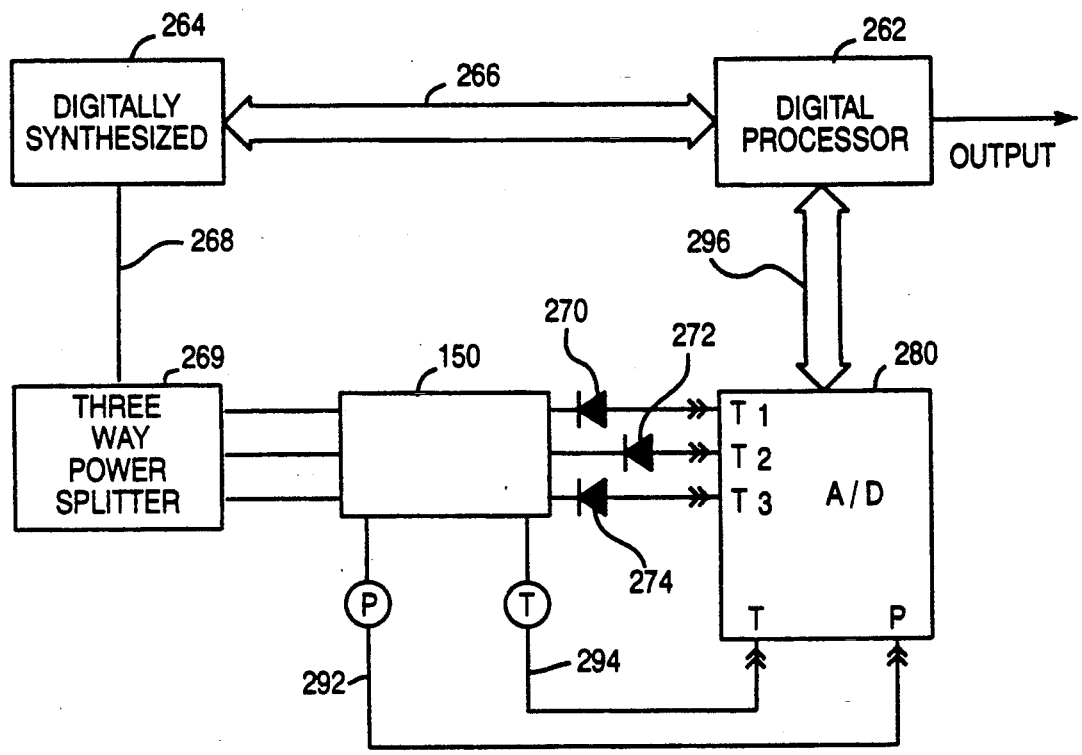
Figure 43:
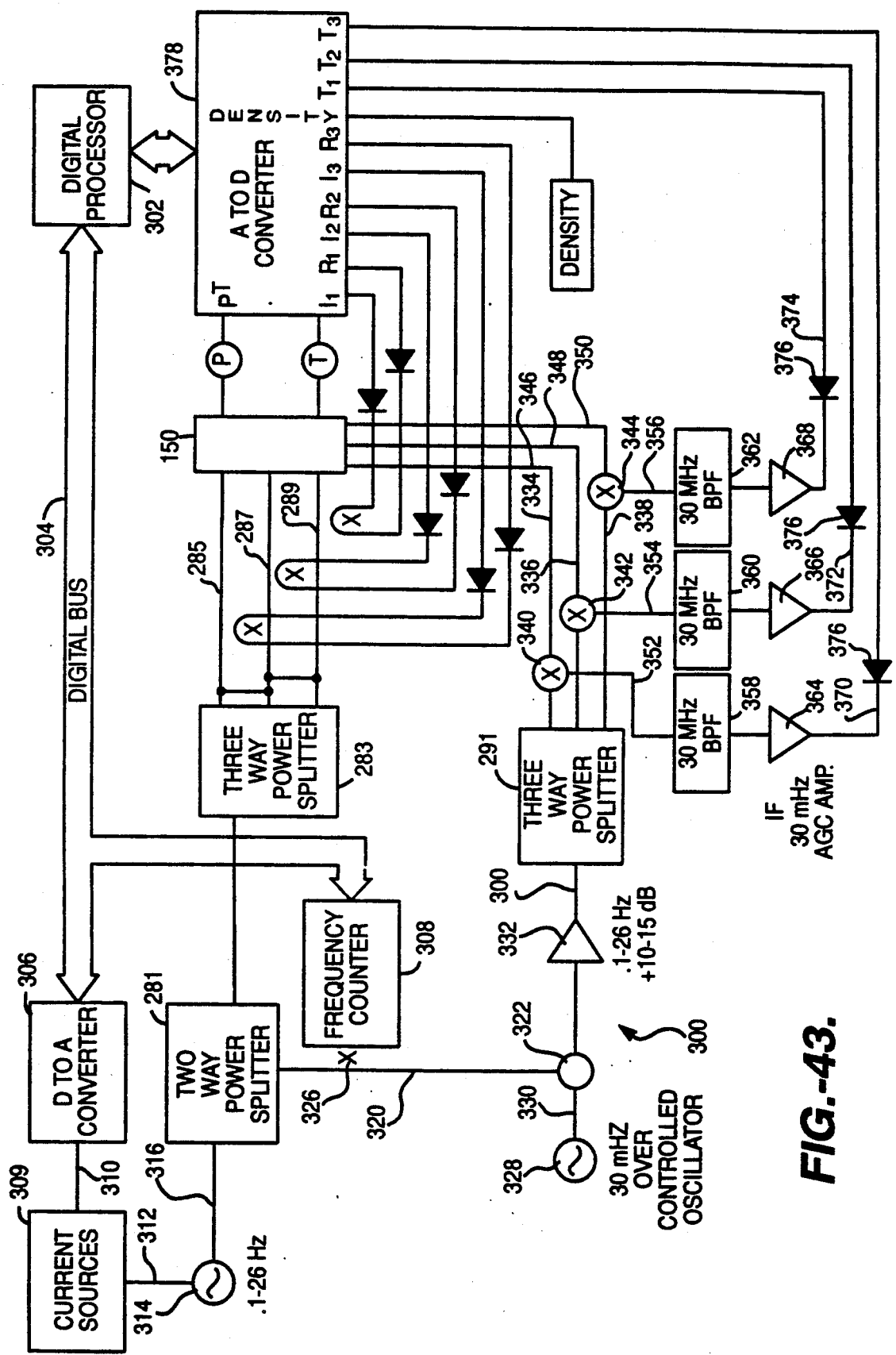

FIGS. 41–43 show various detailed block diagrams of electronics which could be used with transducer 150 when combined with a density measurement means in accordance with the Embodiment 9 concept. The electronics in FIGS. 41 through 43 could be used equally well if either Embodiment 4, 5, and 7 were substituted for Embodiment 6 as shown in FIGS. 39 and 40. Moreover, with suitable modifications for additional transmitting apertures and frequency sources in accordance with the basic electronic designs shown in FIGS. 16 and 17 for operating Embodiments 1-3, these electronics could also be used with Embodiments 1-3. The necessary modifications should be apparent to those skilled in the art.

FIG. 41 shows electronics 200 for use with the monitor transducer 150 to provide a complete monitor suitable for monitoring composition of a three component stream such as oil, water and gas at the wellhead. As in FIG. 25, a digital processor 202 is connected to a digitally synthesized signal generator 204 by a bidirectional controller bus 206. RF output line 208 supplies RF signals on lines 210, 212 and 214 to RF inputs 160, 162 and 164 of the transducer 150. Power splitter 180 divides the RF signals among the lines 210-214. Lines 216 and 218 are coupled to line 210 with directional coupler 220 to supply first incident RF power $I_1$ and reflected RF power $R_1$ inputs as supplied to and received from the transducer 150 to an A/D converter 222 through diodes 224 and 226. Lines 228 and 230 are coupled to line 212 with directional coupler 232 to supply second incident RF power $I_2$ and reflected RF power $R_2$ inputs as supplied to and received from the transducer 150 to the A/D converter 222 through diodes 234 and 236. Lines 238 and 240 are coupled to line 214 at 242 to supply third incident RF power $I_3$ and reflected RF power $R_3$ inputs as supplied to and received from the transducer 150 to the A/D converter 222 through diodes 244 and 246. Similarly, lines 248, 250 and 252 respectively connect the RF outputs 166, 168 and 170 through diodes 273, 275 and 277 to provide first, second and third transmitted RF signals $T_1$, $T_2$ and $T_3$ from the transducer 150 to the A/D converter 222. Lines 254 and 256 connect temperature sensor 172 and pressure sensor 174 to provide flow stream temperature and pressure inputs to the A/D converter 222. Line 258 provides a flow stream density input to the A/D converter 222 from density transducer 176.

The use of the precision digitally controlled signal generator 204 in the FIG. 41 system gives a highly accurate but relatively slow response time multiple component material monitoring system. The FIG. 41 system is especially suited for applications where monitoring accuracy is a primary requirement for materials with a wide range of dielectric properties.

FIG. 42 shows a simpler version of electronics 200. Electronics 260 includes a digital processor 262. The processor 262 is connected to a digitally synthesized source 264 by bus 266. The signal generator 264 is connected to transducer 150 by RF output line 268 through three-way power splitter 269. The transducer 150 is connected through detector diodes 270, 272, and 274 to transmitted power inputs T1, T2, and T3 of A/D converter 280. Temperature and pressure input signals are provided on lines 292 and 294 to the A/D converter 280. Bus 296 connects the A/D converter 280 and the processor 262 for bidirectional communication. Here the incident and reflected energies are not measured. Only the transmitted energy is measured. This version would be most appropriate for monitoring near lossless fluids where the fluid composition does not vary over a wide range and where cost is an important issue. Two such applications are fiscal monitoring of pipeline quality petroleum and steam quality monitoring.

FIG. 43 shows another form of electronics 300 that can be used with composition monitor 150. A digital processor 302 is connected by a digital bus 304 to a digital to analog (D/A) converter 306 and to a frequency counter 308. The D/A converter 306 is connected to a current source 309 by line 310. The current source 309 is connected by line 312 to a 0.1 to 2 GHz frequency sweep RF oscillator 314. Output 316 from the oscillator 314 is supplied to a two-way power splitter 281. Output 318 from the power splitter 281 is supplied to a three-way power splitter 283 and output 320 is supplied to mixer 322. The three-way power splitter is connected to composition monitor 150 by lines 285, 287 and 289. Line 320 is coupled to the frequency counter 308 through coupler 326. The frequency counter 308 forms a feedback loop to compensate for drift in the source 314. An oven controlled stable 30 MHz oscillator 328 is connected to the mixer 322 by line 330. The mixer 322 is connected through a 0.1 Ghz, +10–15 db bandwidth amplifier 332, line 300, a three-way power splitter 291 and lines 334–338 to mixers 340–344. Output lines 346–350 from the monitor 150 are also connected to the mixers 340–344. Outputs 352–356 from the mixers 340-344 are connected through 30 MHz bandpass filters 358-362 to IF 30 MHz automatic gain controlled amplifiers 364-368. Outputs 370-374 from the amplifiers 364-368 are supplied through detector diodes 376 to A/D converter 378. The remaining connections among the inputs to the monitor 150, the monitor 150, the A/D converter 378 and the digital processor 302 are the same as in the FIG. 41 circuits 200, and they therefore will not be described further. Other than as shown and described, the construction and operation of the FIG. 43 embodiment is the same as the FIG. 41 embodiment.

The system of FIG. 43 has both a shorter response time and a lower cost than does the FIG. 41 system because it does not use a precision, broadband digitally controlled signal generator. The system of FIG. 43 is therefore useful for general monitoring applications, where the greater accuracy of the FIG. 41 system is not required.

THE APPLICATION OF THE COMPOSITION MONITORING TECHNOLOGY TO THE FLOW RATE MEASUREMENTS

The method and apparatus of this invention described thus far and illustrated by Embodiments 1-9 are designed to accurately measure the dielectric properties of materials. Because of the physically open structure made possible by the invention, the apparatus of the invention is especially appropriate for measuring materials and mixtures which are moving, i.e. flowing, through the measurement apparatus. The precision and speed with which the dielectric measurements can be made make it possible to configure the various embodiments of this invention in such a way as to measure the flow rate of the material passing through the apparatus. There are two methods by which this can be done.

Figure 44:
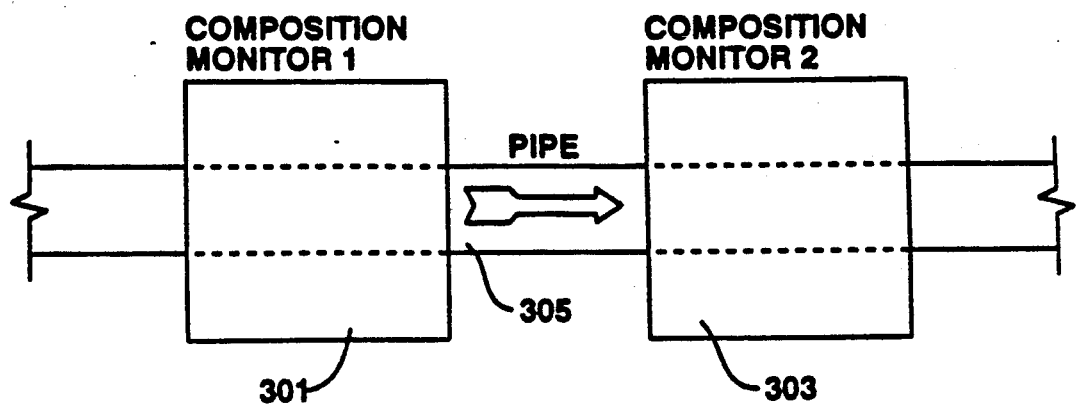
FIGS. 44-45 are schematic side views of flow rate monitoring systems in accordance with the invention.

Embodiment 10—In one embodiment of the flow rate measurement system, as shown in FIG. 44, two composition monitoring devices 301 and 303 are connected by a pipe 305 of known length. The output of these two composition monitoring devices is cross correlated in time to measure the flow rate of the process material. In other words, the time difference is measured during which a given portion of material passes from composition monitor 301 to 303. This time difference and the distance between the composition monitors directly determines the flow rate of the material passing through the system. The particular composition monitor used for this embodiment could be any that is consistent with this invention.

Because the cross correlation technique for flow rate measurement is not a new one, it will not be described in more detail herein. It is important to note, however, that this technique will only work when the material being measured changes its dielectric properties rather dramatically along the process flow line. In fact it works best when there are instantaneous changes such as those that occur under slug flow conditions. If the measured material is evenly mixed and does not change its dielectric properties very abruptly, which is usually the case, then this cross correlation technique would not work. The output of composition monitors 301 and 303 would be essentially identical at all times.

Figure 45:
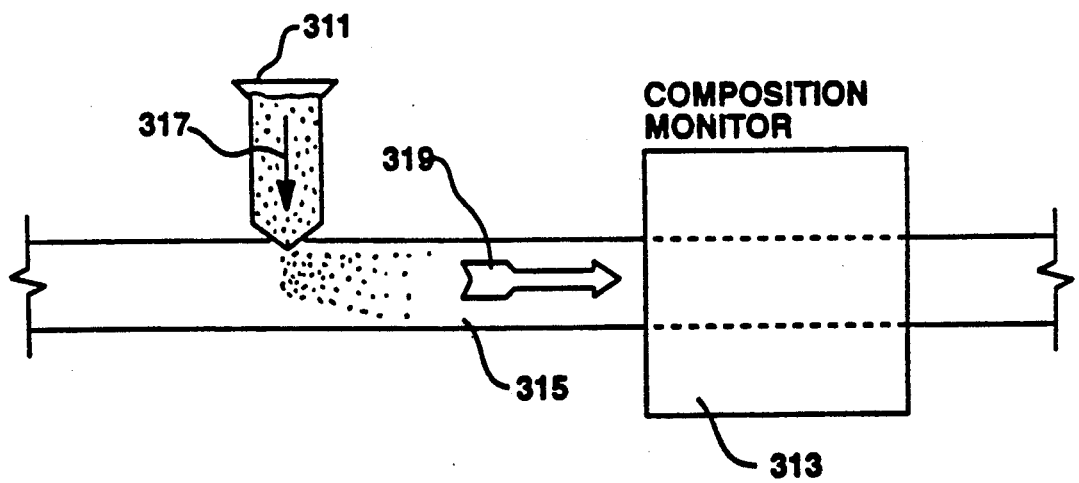

Embodiment 11—A more generally useful technique for measuring the flow rate of a process stream utilizing the material dielectric measuring apparatus of this invention is shown in FIG. 45. In this embodiment, a material injection port or valve 311 is connected upstream of composition monitor 313 by a pipe 315. The distance between the valve 311 and the composition monitor 315 is fixed and known. The injection port 311 is used to inject material 317 into process stream 319 which will modify the dielectric properties of the stream 319 as measured by the composition monitor 313. To measure flow rate, the injection port 311 is used to inject a small slug of material 317 into the stream 319 at time $t_1$. Material 317 must have significantly different dielectric properties than the bulk medium. When the added material 317 is swept through the composition monitor 313, the output of the monitor 313 changes abruptly, signifying its passage. When it passes, the time $t_2$ is noted. The distance between the injection port 311 and the monitor 313 divided by the time difference $t_2 - t_1$ gives the process stream flow rate. The particular composition monitor used for this embodiment could be any that is consistent with this invention.

An example of how this flow rate determination method could be realized is provided by the oil, water, and gas monitoring application. If salty brine is injected into a mixture of oil, water, and gas, then the mixture permittivity and conductivity would increase. The increase could be readily measured by the dielectric measuring apparatus of this invention. More traditional methods of measuring the flow rate of oil, water, and gas such as turbine meters, positive displacement meters, and venturi meters fail because the fluid is two phase (liquid/gas) in nature. Thus the value of the flow rate measurement method described herein is significant.

It should now be readily apparent to those skilled in the art that a novel composition method and apparatus for monitoring the composition of materials and multiple component mixtures capable of achieving the stated objects of the invention has been provided. The method and apparatus of this invention allow for the accurate measurement of the dielectric properties of virtually any material or mixture thereof including solids, liquids, or gases or mixtures of solids/gases, solids/liquids, liquids/gases, liquids/liquids, or solids/liquids/gases. The invention can be used to measure single pieces of test material, batches, or continuously flowing material. The method and apparatus of the invention can be used to measure the composition of materials where the dielectric properties can be related to material composition. When they cannot, the apparatus can still be used as a trend monitor.

The method of the invention uses balanced bridge techniques for RF dielectric measurements in physically open, electrically isolated structures. The physically open structure of the method and apparatus of this invention allows monitoring of materials moving through the measurement apparatus without the apparatus interfering with the material or the material damaging the apparatus. The electrical isolation of the test section of the apparatus reduces or eliminates potential errors that could be caused by reflected interference from other machinery or apparatus outside the test section. The method and apparatus of this invention are designed to produce an electromagnetic interference pattern between two electromagnetic waves propagating in opposite directions in the apparatus. The operating frequency is swept to find characteristic frequencies at which the interference is either constructive or destructive and the measured insertion loss is either a maximum or a minimum. The characteristic frequencies are transduced into fluid permittivity information. This interferometric, balanced bridge technique greatly simplifies the transduction mechanism and improves accuracy. When the conductivity of the measured material is too large, the apparatus instead measures fluid conductivity by measuring insertion loss variations. By measuring fluid properties at locations spaced around the test apparatus, the apparatus determines whether the material being measured is homogeneously mixed. The apparatus utilizes permittivity or conductivity and density measurements to determine composition of three or four component mixtures such as oil, water and gas.

The method and apparatus of this invention can also be used to measure process material flow rates by using either cross correlation techniques implemented with two composition monitors placed a known distance apart in a process stream or by using a single composition monitor placed a known distance downstream of a flow injection device which injects material into the process stream modifying its dielectric properties.

It should further be apparent to those skilled in the art that various changes in form and details of the invention as shown and described may be made. It is intended that such changes be included within the spirit and scope of the claims appended hereto.

What is claimed is:

1. A multiple component composition monitor, which comprises:
    a transducer having an electrically conductive wall forming an enclosure with physically open ends for insertion of the composition, said transducer including a test section having a first end and a second end;
    at least one electromagnetic wave transmission coupler; and
    an electromagnetic wave receiving coupler facing said enclosure;
    said at least one transmission coupler being positioned at a first location on said test section to create electromagnetic waves in said enclosure and said receiving coupler being positioned at a second location on said test section to receive electromagnetic waves from said enclosure;
    said transducer further including an impedance section at each of said first and second ends of said test section, each said impedance section having an impedance different from an impedance of said test section;
    a circuit in which said transducer comprises at least one electrical path in said circuit; and
    means for producing a minimum or maximum output from said circuit by inducing an electromagnetic interference pattern, said minimum or maximum output serving to characterize relative proportions of the components in the composition.

2. The multiple component composition monitor of claim 1 in which each said impedance section for terminating said test section comprises at least one physical discontinuity in said electrically conductive wall.

3. The multiple component composition monitor of claim 2 in which each said physical discontinuity in said electrically conductive wall comprises at least one portion of said electrically conductive wall having a greater cross section than remainder of said electrically conductive wall.

4. The multiple component composition monitor of claim 3 in which each said physical discontinuity lies substantially in a plane transverse to a longitudinal dimension of the enclosure.

5. The multiple component composition monitor of claim 1 in which said transmitting and receiving couplers are positioned in said electrically conductive wall.

6. The multiple component composition monitor of claim 1, in which:
    said at least one electromagnetic wave transmission coupler comprises a plurality of electromagnetic wave transmitting apertures, and said at least one electromagnetic wave receiving coupler comprises a plurality of electromagnetic wave receiving apertures, said transmitting and receiving apertures being positioned around said electrically conductive wall.

7. The multiple component composition monitor of claim 1 in which said at least one transmission coupler comprises at least a first transmitting coupler and a second transmitting coupler, wherein said receiving coupler is positioned at a different distance from said first transmitting coupler than from said second transmitting coupler.

8. The multiple component composition monitor of claim 1, further including means external to said test section for splitting an input signal to said test section into first and second signal portions, wherein said circuit comprises a bridge circuit serving to balance the first and second signal portions, said means for splitting the input signal being connected to pass at least one said first signal portion through said test section, and said means for producing a minimum or maximum output from said circuit being connected to receive said second signal portion for tuning said circuit to produce the maximum or minimum.

9. The multiple component composition monitor of claim 8 in which said test section including a substantially lossless waveguide material and said impedance section includes a lossy waveguide material at each of said first and second ends of said test section.

10. The multiple component composition monitor of claim 8 in which said means for producing a minimum output from said bridge circuit includes means for obtaining a transmission phase difference of 180 degrees between said first and second signal portions.

11. The multiple component composition monitor of claim 8 in which said means for producing a minimum output from said bridge circuit includes means for adjusting a transmission property of the second signal portion to produce a null output.

12. The multiple component composition monitor of claim 11, in which said means for adjusting a transmission property of the second signal portion includes means for adjusting attenuation of said second signal portion.

13. The multiple component composition monitor of claim 11, in which said means for adjusting a transmission property of the second signal portion includes means for adjusting phase of the second signal portion.

14. The multiple component composition monitor of claim 11, in which said means for adjusting a transmission property of the second signal portion includes means for adjusting phase and attenuation of the second signal portion.

15. The multiple component composition monitor of claim 8, wherein said circuit is configured for passing said first and second signal portions through said test section, and for passing said second signal portion but not said first signal portion through said means for producing a minimum or maximum output.

16. The multiple component composition monitor of claim 15, wherein said means for producing a minimum or maximum output includes a frequency generator connected for providing said input signal to said signal splitting means, and means for adjusting frequency of said second signal portion.

17. The multiple component composition monitor of claim 16, wherein said means for producing a minimum or maximum output further comprises a variable resistor connected for adjusting attenuation of said second signal portion.

18. The multiple component composition monitor of claim 8, wherein said impedance section comprises a lossy load section connected to each of said first and second ends of said test section.

19. The multiple component composition monitor of claim 8, wherein said means for producing a minimum or maximum output includes a variable frequency generator connected for providing said input signal to said signal splitting means, and a variable resistor connected for adjusting attenuation of said second signal portion.

20. The multiple component composition monitor of claim 8, wherein said means for producing a minimum or maximum output includes a variable resistor and a phase adjustor connected for adjusting attenuation and phase, respectively, of said second signal portion.

21. The multiple component composition monitor of claim 1 additionally comprising a means connected to said at least one transmitting coupler for varying frequency of the electromagnetic waves.

22. The multiple component composition monitor of claim 1 in which said enclosure includes a passage adapted for flowing the composition therethrough.

23. The multiple component composition monitor of claim 1, said monitor constituting a first monitor mounted at a first location on a pipe for flowing said composition therethrough, wherein a second multiple component composition monitor in accordance with claim 1 is mounted at a second location on said pipe at a distance from said first location, and wherein said first and second monitors in combination constitute means for determining a flow rate of the composition through said pipe, further including means connected to said first and second monitors for cross-correlating output signals from said multiple component composition monitor and said second composition monitor for determining a length of time taken for a portion of the composition to travel from said first location to said second location.

24. The multiple component composition monitor of claim 1, wherein a material injection port is mounted on said pipe at a known distance upstream from said multiple component composition monitor, wherein said composition monitor and material injection port in combination constitute means for determining a flow rate of the composition through said pipe, said flow rate determining means further including means for measuring an amount of time taken for material injected at said material injection port to travel to said multiple component composition monitor.

25. The multiple component composition monitor of claim 1 in which said circuit comprises a bridge circuit having a first electrical path and a second electrical path, said second electrical path including adjustable circuit elements external of said transducer.

26. The multiple component composition monitor of claim 25, in which the adjustable circuit elements comprise a variable attenuator.

27. The multiple component composition monitor of claim 25, in which the adjustable circuit element comprises a variable phase shifter.

28. The multiple component composition monitor of claim 1, in which said circuit constitutes a bridge circuit and said transducer comprises two electrical paths in said bridge circuit.

29. The multiple component composition monitor of claim 1, further including a density monitor connected to said transducer at a location spaced from said test section for measuring density of the composition.

30. The multiple component composition monitor of claim 29, further including means coupled to said density monitor for comparing said measured density with a calculated density for the composition.

31. A multiple component composition monitor, comprising:
    a transducer having an electrically conductive wall forming an enclosure with physically open ends for insertion of the composition, said transducer including a test section having a first end and a second end;
    at least one electromagnetic wave transmission coupler; and
    an electromagnetic wave receiving coupler facing said enclosure;
    said at least one transmission coupler being positioned to create electromagnetic waves in said enclosure and said receiving coupler being positioned to receive electromagnetic waves from said enclosure;
    said at least one transmission coupler and said receiving coupler being located in said test section;
    said transducer further including an impedance section at each of said first and second ends of said test section, each said impedance section having an impedance different from an impedance of said test section;
    a circuit in which said transducer comprises at least one electrical path in said circuit; and
    means for producing a minimum or maximum output from said circuit by inducing an electromagnetic interference pattern, said minimum or maximum output serving to characterize relative proportions of the components in the composition;
    in which said impedance section comprises a sleeve of insulating material positioned on an inside source of said electrically conductive wall, said sleeve of insulating material having a first portion of a first insulating material adjacent said transmitting and receiving couplers, said sleeve of insulating material having second portions of a second insulating material, with one said second portion joined to said first portion on each side of said transmitting and receiving couplers, the second insulating material having a substantially different dielectric constant than the first insulating material.

32. A multiple component composition monitor, comprising:
    a transducer having an electrically conductive wall forming an enclosure with physically open ends for insertion of the composition, said transducer including a test section having a first end and a second end;
    at least one electromagnetic wave transmission coupler; and
    an electromagnetic wave receiving coupler facing said enclosure;

said at least one transmission coupler being positioned to create electromagnetic waves in said enclosure and said receiving coupler being positioned to receive electromagnetic waves from said enclosure;

said at least one transmission coupler and said receiving coupler being located in said test section;

said transducer further including an impedance section at each of said first and second ends of said test section, each said impedance section having an impedance different from an impedance of said test section;

a circuit in which said transducer comprises at least noe electrical path in said circuit; and means for producing a minimum or maximum output from said circuit by inducing an electromagnetic interference pattern, said minimum or maximum output serving to characterize relative proportions of the components in the composition;

in which said impedance section comprises portions of said electrically conductive wall positioned on either side of said test section, wherein said test section has a cutoff frequency different from a cutoff frequency of said impedance section.

33. The multiple component composition monitor of claim 32 additionally comprising an insulating sleeve extending through the first portion and the second portions of said electrically conductive wall.

34. The multiple component composition of claim 32, wherein said test section has a perimeter that is noncoextensive with a perimeter of said impedance section.

35. The multiple component composition of claim 34, wherein said test section has a different size than said impedance section.

36. The multiple component composition of claim 34, wherein said test section has a different shape than said impedance section.

37. The multiple component composition of claim 34, wherein said test section has a different geometrical arrangement than said impedance section.

38. The multiple component composition of claim 34, wherein said test section has a different diameter than said impedance section.

39. The multiple component composition of claim 38, wherein said test section has a larger diameter than said impedance section.

40. The multiple component composition of claim 38, wherein said test section has a smaller diameter than said impedance section.

41. A multiple component composition monitor, comprising:

a transducer having an electrically conductive wall forming an enclosure with physically open ends for insertion of the composition, said transducer including a test section having a first end and a second end;

at least one electromagnetic wave transmission coupler; and an electromagnetic wave receiving coupler facing said enclosure;

said at least one transmission coupler being positioned to create electromagnetic waves in said enclosure and said receiving coupler being positioned to receive electromagnetic waves from said enclosure;

said at least one transmission coupler and said receiving coupler being located in said test section;

said transducer further including an impedance section at each of said first and second ends of said test section, each said impedance section having an impedance different from an impedance of said test section;

a circuit in which said transducer comprises at least noe electrical path in said circuit; and means for producing a minimum or maximum output from said circuit by inducing an electromagnetic interference pattern, said minimum or maximum output serving to characterize relative proportions of the components in the composition;

in which said impedance section comprises a waveguide reactive load section connected to each of said first and second ends of said test section, said waveguide reactive load sections being generally parallel to a longitudinal dimension of said test section and segmented by a plurality of metal surfaces.

42. A multiple component composition monitor transducer, which comprises:

an electrically conductive wall forming an enclosure for the composition;

at least a pair of electromagnetic wave transmission couplers and an electromagnetic wave receiving coupler facing said enclosure;

said at least a pair of transmission couplers being positioned to create interfering electromagnetic waves in said enclosure and said receiving coupler being positioned to receive electromagnetic waves from said enclosure; and means for electrically isolating a test section of said transducer, wherein said transducer includes said at least a pair of transmission couplers and said receiving coupler.

43. The multiple component composition monitor of claim 42, in which said at least a pair of transmission couplers are spaced different distances from said receiving coupler.

44. The multiple component composition monitor of claim 42, in which said means for electrically isolating said test section comprises a substantially lossless waveguide material positioned in said test section and a lossy waveguide material positioned at each of two ends of said test section.

45. The multiple component composition monitor of claim 42, in which said enclosure includes a passage for flowing the composition therethrough.

46. A process for measuring the composition of a multiple component mixture, including the steps of:

(1) providing at least one electromagnetic wave transmitting coupler at a distance from a receiving coupler;

(2) transmitting elector magnetic waves into the mixture;

(3) generating an interference pattern of the electromagnetic waves in the mixture;

(4) receiving the transmitted electromagnetic waves at the receiving coupler;

(5) varying the frequency of the electromagnetic waves; and (6) observing frequencies at which transmitted energy maxima or minima are received.

47. The process of claim 30 additionally comprising the step of measuring density of the multiple component mixture.

48. The process of claim 46 in which the electromagnetic waves are transmitted and received at a plurality of points around a test section enclosing the mixture.

49. The process of claim 46, additionally comprising, during the steps 2 through 6, the step of flowing the mixture past the transmission couplers and the receiving coupler.

50. The process of claim 46 additionally comprising the step of isolating the transmission and receiving couplers with a load on each side of the transmission couplers remote from the receiving coupler.

51. The process of claim 50, wherein the load is a reactive load.

52. The process of claim 50, wherein the load is a resistive load.

53. The process of claim 46 additionally comprising the step of determining flow rate of the multiple component mixture.

54. The process of claim 53, wherein steps 1 through 6 are carried out at a first location at a first time, and comprise a first composition measurement, and wherein the flow rate determining step includes the steps of:
   generating a second composition measurement by measuring the composition of the multiple component mixture in accordance with claim 30 at a second time at a second location spaced from the first location; and
   cross-correlating the first and second composition measurements.

55. The process of claim 53, wherein steps 1 through 6 are carried out at a first location, and the flow rate determining step includes the steps of:
   injecting a material into the multiple component mixture at a second location a known distance from the first location; and
   determining the flow rate from travel time of the injected material from the second location to the first location.

56. The multiple component composition monitor of claim 22, including means coupled to said passage for determining a flow rate of the composition therethrough.

57. A multiple component composition monitor for measuring ratios of component materials in a composition, comprising:
   a transducer having an electrically conductive wall forming an enclosure for receiving the composition, said transducer including a test section having a first end, a second end, and an impedance section at each of said first and second ends, each of said impedance section having an impedance different from an impedance of said test section;
   at least one electromagnetic wave transmission coupler; positioned at said test section for creating electromagnetic waves in said enclosure;
   an electromagnetic wave receiving coupler positioned at said test section for receiving said electromagnetic waves from said enclosure;
   a circuit in which said transducer comprises at least one electrical path in said circuit;
   means for producing a minimum or maximum output from said circuit by inducing an electromagnetic interference pattern; and
   a density monitor connected to said transducer for measuring density of the composition, said minimum or maximum output and said density serving to characterize the ratios of the components materials in the composition.

58. The multiple component composition monitor of claim 57, in which said enclosure includes a passage adapted for flowing the composition therethrough.

59. The multiple component composition monitor of claim 58, including means coupled to said passage for determining a flow rate of the composition therethrough.

60. The multiple component composition monitor of claim 57, said monitor constituting a first monitor mounted at a first location on a pipe for flowing said composition therethrough, wherein a second multiple component composition monitor in accordance with claim 68 is mounted at a second location on said pipe at a distance from said first location, and wherein said first and second monitors in combination constitute means for determining a flow rate of the composition through said pipe, further including means connected to said first and second monitors for cross-correlating output signals from said multiple component composition monitor and said second composition monitor for determining a length of time taken for a portion of the composition to travel from said first location to said second location.

61. The multiple component composition monitor of claim 57, wherein a material injection port is mounted on said pipe at a known distance upstream from said multiple component composition monitor, wherein said composition monitor and material injection port in combination constitutes means for determining a flow rate of the composition through said pipe, said flow rate determining means further including means for measuring an amount of time taken for material injected by at said material injection port to travel to said multiple component composition monitor.

* * * * *

UNITED STATES PATENT AND TRADEMARK OFFICE
CERTIFICATE OF CORRECTION

PATENT NO. : 5,103,181
DATED : April 7, 1992
INVENTOR(S) : Scott G. Gaisford, John P. Watjen and Bjorn G. Bjornsen It is certified that error appears in the above-indentified patent and that said Letters Patent is hereby corrected as shown below:

On the title page, item [73] Assignee, after "Norske" insert --Stats--; and delete "Stavonger" and substitute therefor --Stavanger--.
In item [57] Abstract, line 19, delete "comiponent" and substitute therefor --component--; and line 20, delete "strams" and substitute therefor --streams--.

Col. 10, line 31, delete "-", second occurrence.
Col. 19, line 46, after "47", add --48--.
Col. 23, line 65, delete "component" after "volumeteric".
Col. 24, line 20, delete "electric" and substitute therefor --dielectric--.
Col. 33, line 13, deelete "noe" and substitute therefor --one--.
Col. 34, line 4, delete "noe" and substitute therefor --one.
Col. 36, line 45, delete "constitutes" and substitute therefor --constitute--.

Signed and Sealed this

Seventeenth Day of May, 1994

BRUCE LEHMAN

Attest:

Attesting Officer    Commissioner of Patents and Trademarks